(12) United States Patent
Park et al.

(10) Patent No.: US 11,835,536 B2
(45) Date of Patent: *Dec. 5, 2023

(54) DEVICE AND METHOD FOR QUALITATIVE AND QUANTITATIVE ANALYSIS OF HEAVY METALS UTILIZING ROTARY DISC SYSTEM

(71) Applicant: LG Chem, Ltd., Seoul (KR)

(72) Inventors: Byung Hyun Park, Daejeon (KR); Byoung Hyoun Kim, Daejeon (KR); Dong Hyun Kim, Daejeon (KR); Su Youn Han, Daejeon (KR)

(73) Assignee: LG Chem, Ltd.

(*) Notice: Subject to any disclaimer, the term of this patent is extended or adjusted under 35 U.S.C. 154(b) by 222 days.

This patent is subject to a terminal disclaimer.

(21) Appl. No.: 16/638,350

(22) PCT Filed: Oct. 25, 2018

(86) PCT No.: PCT/KR2018/012738
§ 371 (c)(1),
(2) Date: Feb. 11, 2020

(87) PCT Pub. No.: WO2019/098536
PCT Pub. Date: May 23, 2019

(65) Prior Publication Data
US 2020/0254449 A1  Aug. 13, 2020

(30) Foreign Application Priority Data

Nov. 20, 2017 (KR) .................. 10-2017-0154395
May 10, 2018 (KR) .................. 10-2018-0053639

(51) Int. Cl.
*G01N 21/78* (2006.01)
*G01N 31/22* (2006.01)
(Continued)

(52) U.S. Cl.
CPC ........ *G01N 35/1095* (2013.01); *B01L 3/5027* (2013.01); *B01L 3/50273* (2013.01);
(Continued)

(58) Field of Classification Search
CPC .... G01N 35/1095; G01N 21/78; G01N 31/22; G01N 33/20; G01N 35/08;
(Continued)

(56) References Cited

U.S. PATENT DOCUMENTS 5,075,215 A    12/1991  Dreyer
7,723,120 B2   5/2010   Xiao et al.
(Continued)

FOREIGN PATENT DOCUMENTS

CN    101748204 A    6/2010
CN    102580644 A    7/2012
(Continued)

OTHER PUBLICATIONS

European Search Report for Application No. EP18878488.8, dated Nov. 4, 2020, 10 pages.
(Continued)

*Primary Examiner* — Matthew D Krcha
*Assistant Examiner* — Sophia Y Lyle
(74) *Attorney, Agent, or Firm* — Lerner David LLP

(57) ABSTRACT

The present invention relates to a device and a method for qualitative and quantitative analysis of heavy metals and more particularly provides a device and a method for qualitative and quantitative analysis of heavy metals utilizing a rotary disc system.

13 Claims, 24 Drawing Sheets

(51) Int. Cl.
  *G01N 21/75* (2006.01)
  *G01N 21/77* (2006.01)
  *G01N 35/10* (2006.01)
  *G01N 35/08* (2006.01)
  *B01L 3/00* (2006.01)
  *G01N 33/20* (2019.01)

(52) U.S. Cl.
  CPC ........ *B01L 3/502715* (2013.01); *G01N 21/78* (2013.01); *G01N 31/22* (2013.01); *G01N 33/20* (2013.01); *G01N 35/08* (2013.01); *B01L 2200/16* (2013.01); *B01L 2300/06* (2013.01); *B01L 2300/0803* (2013.01); *B01L 2300/126* (2013.01); *B01L 2300/16* (2013.01); *B01L 2400/0475* (2013.01)

(58) Field of Classification Search
  CPC ....... G01N 35/00069; G01N 2021/757; G01N 2035/00158; G01N 21/07; G01N 35/085; G01N 2021/7759; B01L 3/5027; B01L 3/502715; B01L 3/50273; B01L 2200/16; B01L 2300/06; B01L 2300/0803; B01L 2300/126; B01L 2300/16; B01L 2400/0475; B01L 2200/0684; B01L 3/00; B01L 3/5023; B01L 2300/028; B01L 2300/069; B01L 2300/0825; B01L 2300/0861; B01L 2300/087; B01L 2400/0409; B01L 2200/10; B01L 2300/0636
  See application file for complete search history.

(56) References Cited

U.S. PATENT DOCUMENTS

| | | | |
|---|---|---|---|
| 8,191,715 B2 | 6/2012 | Cho et al. | |
| 8,470,588 B2 | 6/2013 | Boehm et al. | |
| 9,737,889 B2 | 8/2017 | Moon et al. | |
| 9,737,890 B2 | 8/2017 | Lin et al. | |
| 2001/0001060 A1* | 5/2001 | Kellogg | B01L 3/502738 435/7.1 |
| 2003/0203495 A1* | 10/2003 | Rupp | G01N 31/22 422/423 |
| 2004/0161365 A1 | 8/2004 | Siu Yu | |
| 2005/0059165 A9* | 3/2005 | Davis | B01L 3/0217 436/514 |
| 2005/0087479 A1* | 4/2005 | Okada | G01N 35/00069 210/512.1 |
| 2005/0250218 A1 | 11/2005 | Andrelczyk et al. | |
| 2008/0227217 A1 | 9/2008 | Yamamoto et al. | |
| 2008/0280365 A1 | 11/2008 | Grumann et al. | |
| 2009/0191643 A1 | 7/2009 | Boehm et al. | |
| 2010/0120173 A1 | 5/2010 | Zhou et al. | |
| 2010/0297659 A1* | 11/2010 | Yoo | B01L 3/502753 435/6.16 |
| 2012/0178182 A1 | 7/2012 | Kim et al. | |
| 2012/0282707 A1 | 11/2012 | Borch | |
| 2014/0017806 A1 | 1/2014 | Lee | |
| 2014/0178978 A1* | 6/2014 | Cate | G01N 21/78 422/402 |
| 2014/0186935 A1 | 7/2014 | Yoo | |
| 2014/0199776 A1 | 7/2014 | Kim et al. | |
| 2014/0370502 A1 | 12/2014 | Brennan et al. | |
| 2015/0064774 A1 | 3/2015 | Moon et al. | |
| 2015/0254845 A1* | 9/2015 | Tsai | G06V 10/56 382/128 |
| 2015/0321192 A1 | 11/2015 | Lee | |
| 2016/0051986 A1 | 2/2016 | Lin et al. | |
| 2017/0023465 A1* | 1/2017 | Zehler | G01N 21/78 |
| 2017/0209863 A1 | 7/2017 | Qin et al. | |
| 2018/0369812 A1 | 12/2018 | Boehm et al. | |
| 2019/0004043 A1 | 1/2019 | Araoz et al. | |
| 2020/0141962 A1 | 5/2020 | Park et al. | |

FOREIGN PATENT DOCUMENTS

| | | | | |
|---|---|---|---|---|
| CN | 103537329 A | | 1/2014 | |
| CN | 103917638 A | | 7/2014 | |
| CN | 104360068 A | | 2/2015 | |
| CN | 104937415 A | | 9/2015 | |
| CN | 105445449 A | * | 3/2016 | |
| CN | 107192709 A | | 9/2017 | |
| EP | 2026072 A1 | | 2/2009 | |
| EP | 3173149 A1 | | 5/2017 | |
| EP | 3715852 A1 | | 9/2020 | |
| EP | 3715853 A1 | | 9/2020 | |
| GB | 2386331 A | * | 9/2003 | ............ B01L 3/0268 |
| JP | 2003028883 A | | 1/2003 | |
| JP | 2004021112 A | | 1/2004 | |
| JP | 2007078676 A | | 3/2007 | |
| JP | 2007278741 A | | 10/2007 | |
| JP | 2007052647 A1 | | 4/2009 | |
| JP | 2010505096 A | | 2/2010 | |
| JP | 2013156070 A | | 8/2013 | |
| JP | 2015531494 A | | 11/2015 | |
| JP | 2019513977 A | | 5/2019 | |
| JP | 2020522704 A | | 7/2020 | |
| JP | 2020522705 A | | 7/2020 | |
| KR | 20030046315 A | | 6/2003 | |
| KR | 20080047409 A | | 5/2008 | |
| KR | 100846516 B1 | | 7/2008 | |
| KR | 20080069209 A | | 7/2008 | |
| KR | 20110079570 A | | 7/2011 | |
| KR | 20120132477 A | | 12/2012 | |
| KR | 2013000009 A | * | 1/2013 | |
| KR | 20130000009 A | | 1/2013 | |
| KR | 101256474 B1 | | 4/2013 | |
| KR | 20130107069 A | | 10/2013 | |
| KR | 20140008976 A | | 1/2014 | |
| KR | 101375752 B1 | | 3/2014 | |
| KR | 20150027939 A | | 3/2015 | |
| KR | 20160022751 A | | 3/2016 | |
| KR | 20160105729 A | | 9/2016 | |
| KR | 20160119425 A | | 10/2016 | |
| KR | 20170024274 A | | 3/2017 | |
| WO | 2017108582 A1 | | 6/2017 | |

OTHER PUBLICATIONS

European Search Report for Application No. EP18879636.1, dated Nov. 9, 2020, 10 pages.
Extended European Search Report including Written Opinion for EP18878218.9, dated Nov. 4, 2020, 10 pages.
International Search Report from Application No. PCT/KR2018/012724, dated Feb. 11, 2019, 2 pages.
International Search Report from Application No. PCT/KR2018/012732 dated Feb. 11, 2019, 2 pages.
International Search Report from Application No. PCT/KR2018/012736 dated Feb. 11, 2019, 2 pages.
International Search Report from Application No. PCT/KR2018/012738 dated Feb. 11, 2019, 3 pages.
Extended European Search Report including Written Opinion for EP18877790.8 dated Oct. 5, 2020; 9 pages.
Search Report dated Aug. 10, 2022 from the Office Action for Chinese Application No. 201880037193.4 dated Aug. 17, 2022, 3 pages.
Search Report dated Aug. 17, 2022 from the Office Action for Chinese Application No. 201880036885.7 dated Aug. 24, 2022, 3 pages.
Search Report dated Aug. 17, 2022 from the Office Action for Chinese Application No. 201880037187.9 dated Aug. 23, 2022, 3 pages.
Search Report dated Aug. 19, 2022 from the Office Action for Chinese Application No. 201880036599.0 dated Aug. 26, 2022, 3 pages.

* cited by examiner

[FIG. 1A]
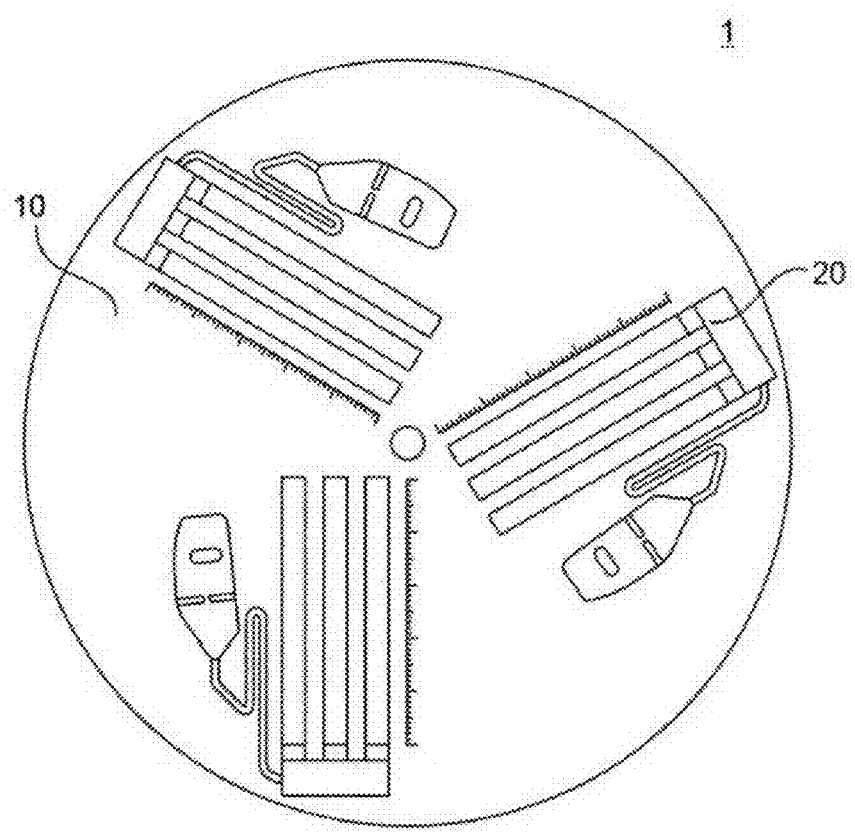

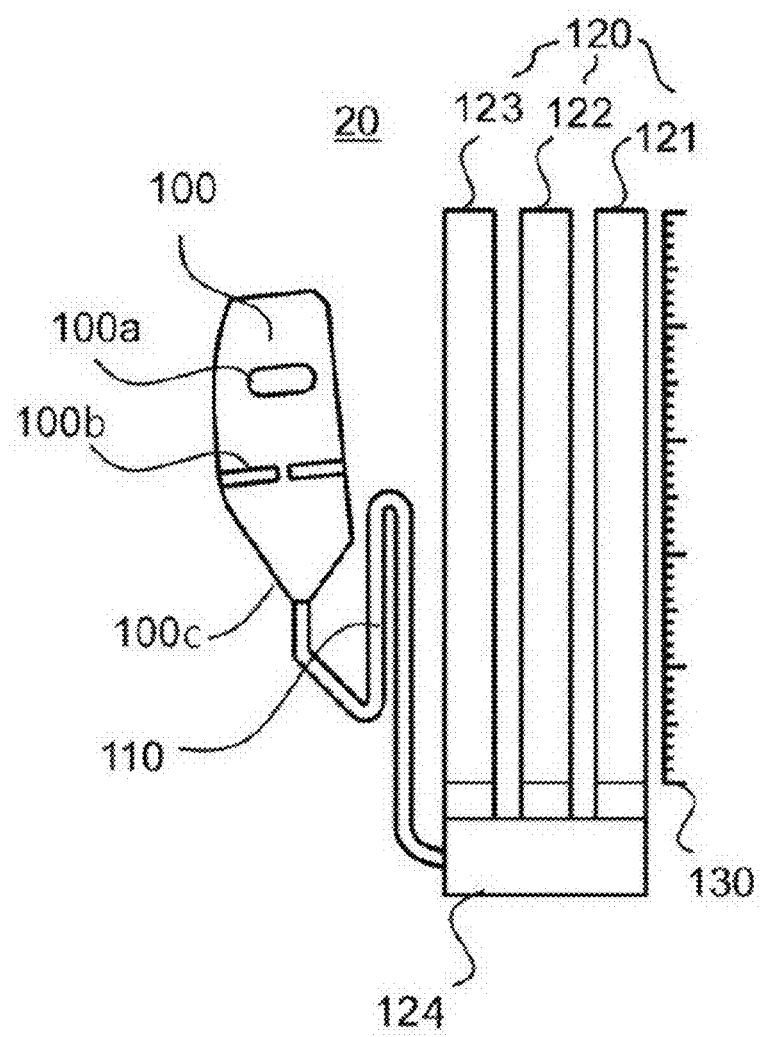
[FIG. 1B]

[FIG. 1C]
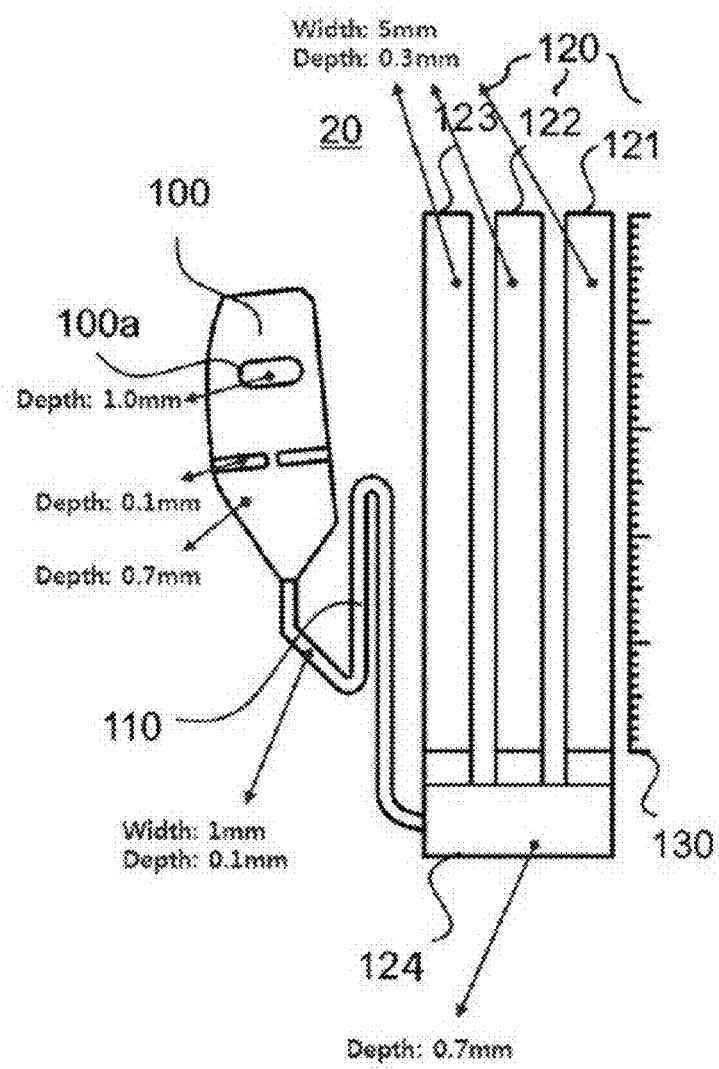

[FIG. 1D]
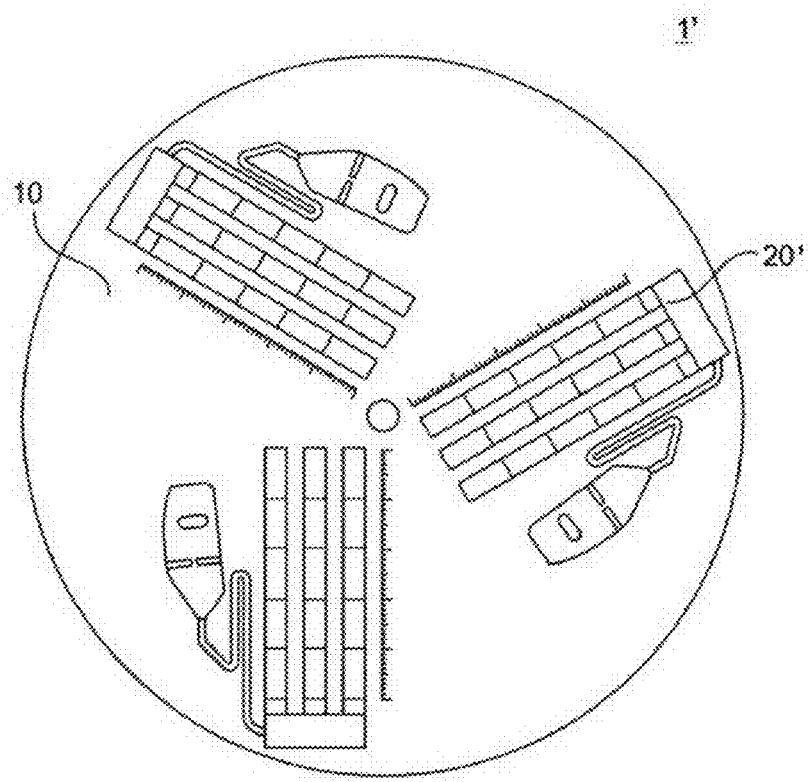

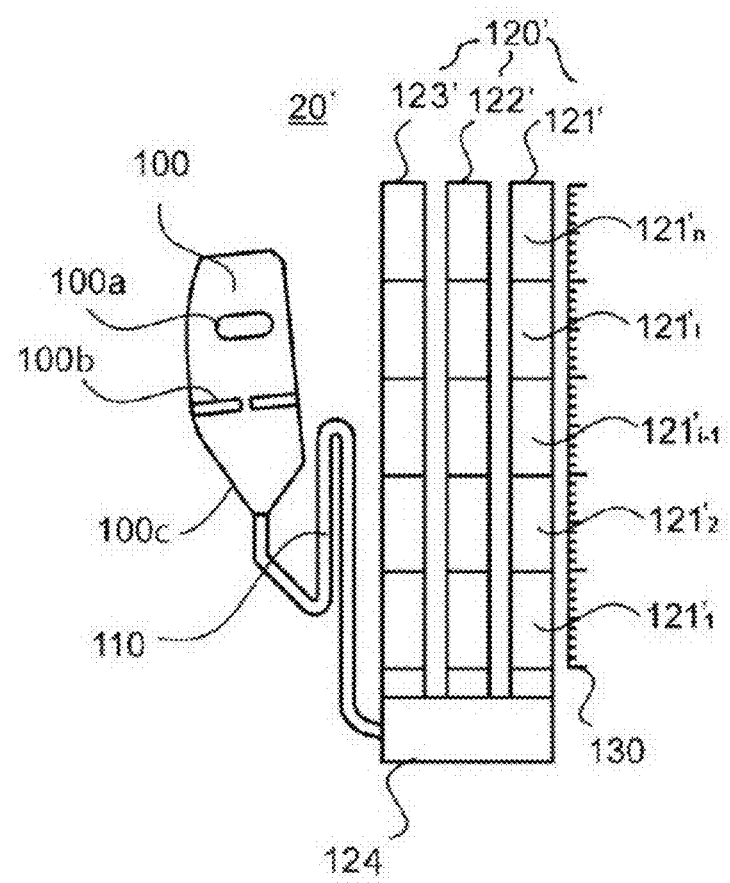
[FIG. 1E]

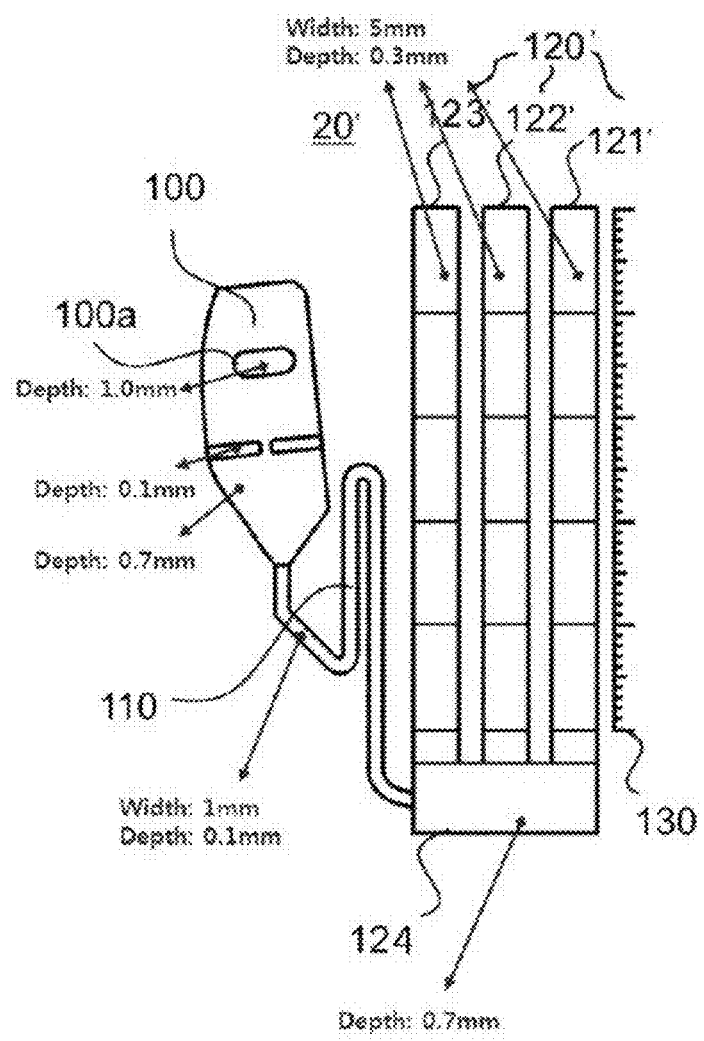
[FIG. 1F]

[FIG. 1G]
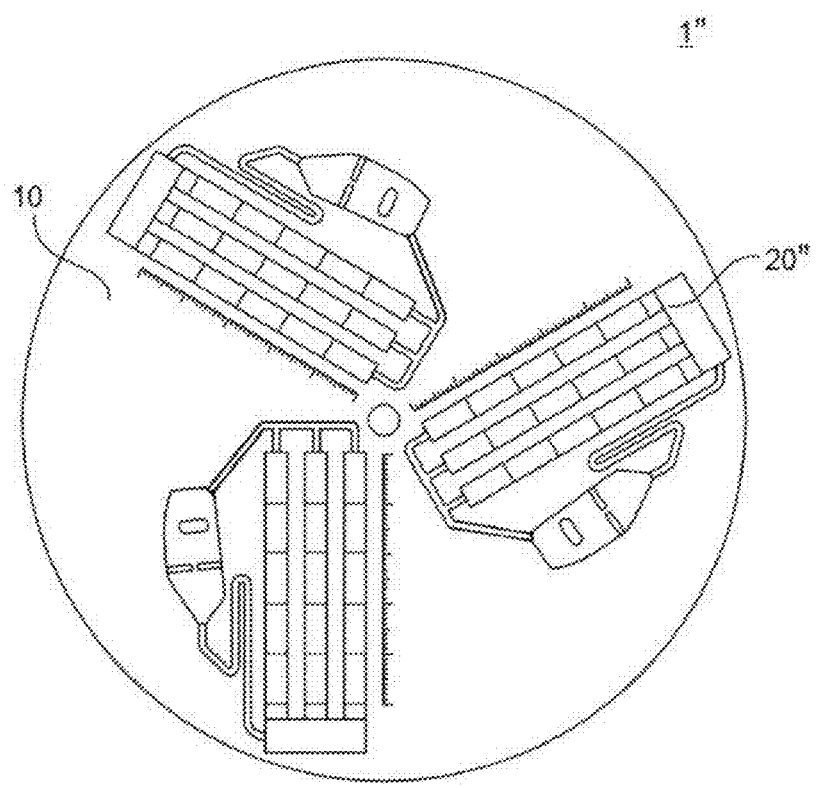

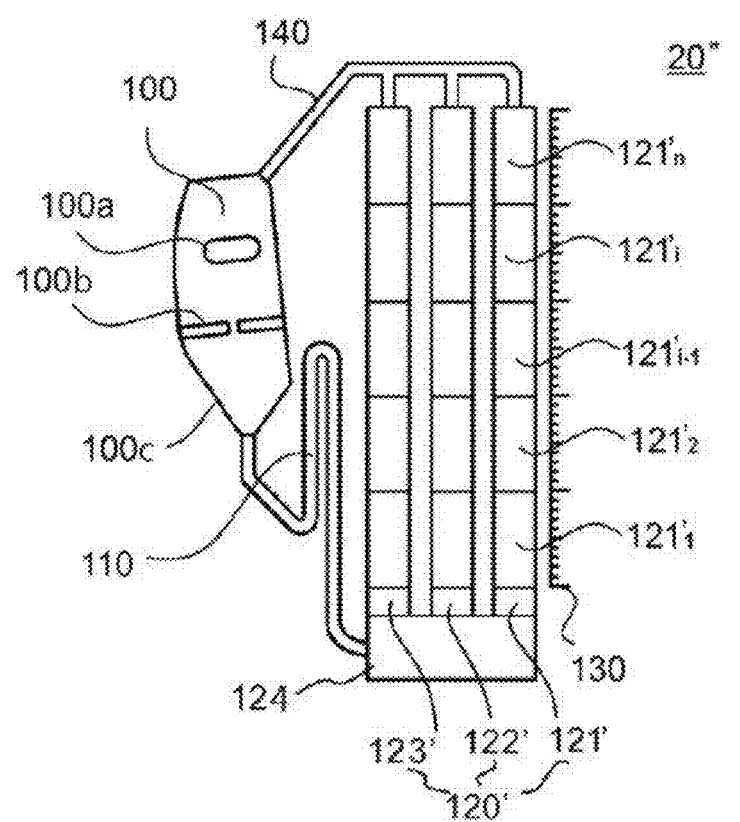
[FIG. 1H]

[FIG. 1I]
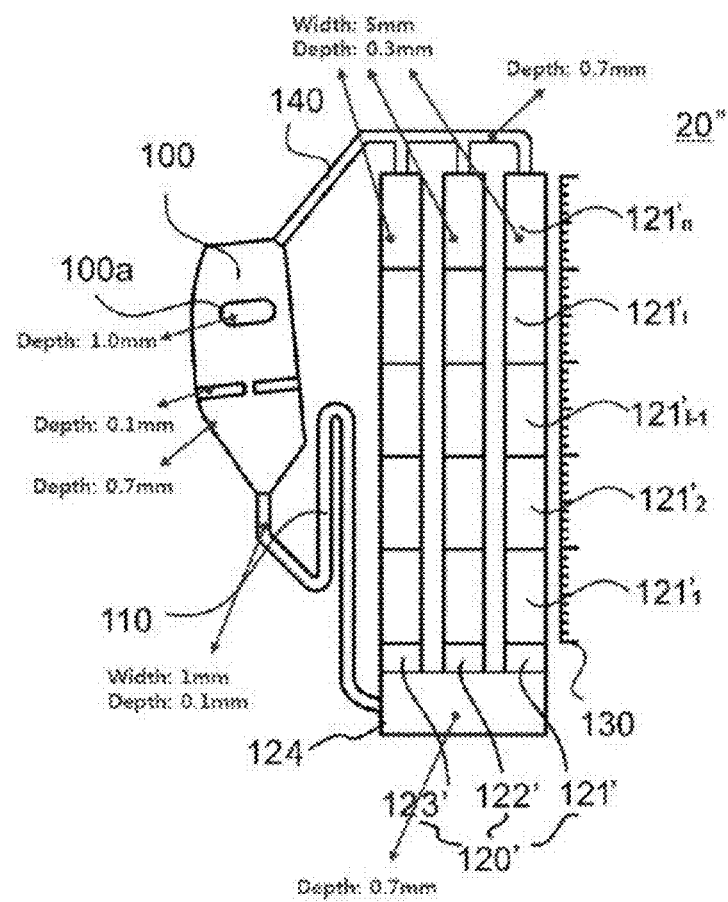

[FIG. 2A]
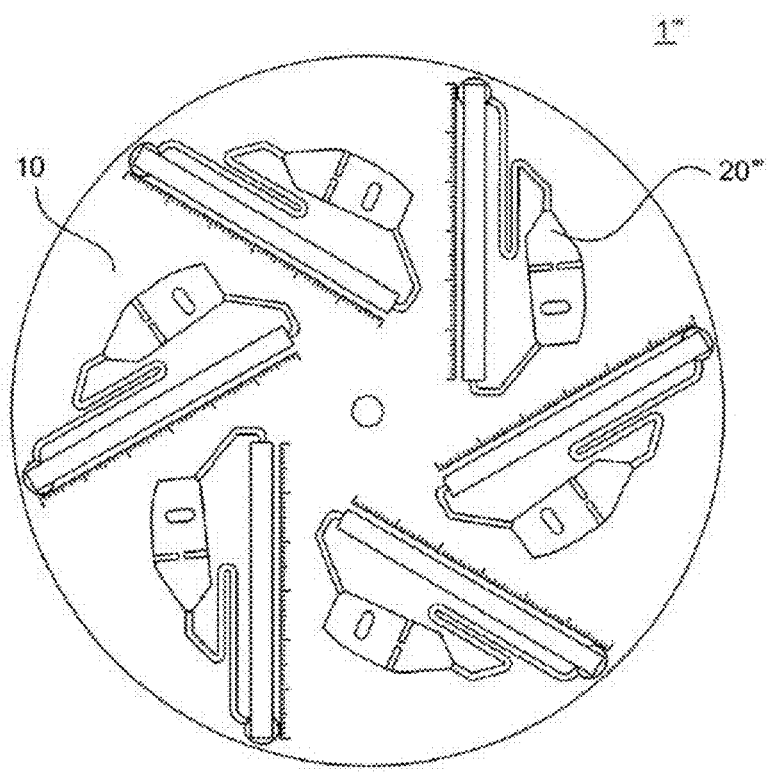

[FIG. 2B]
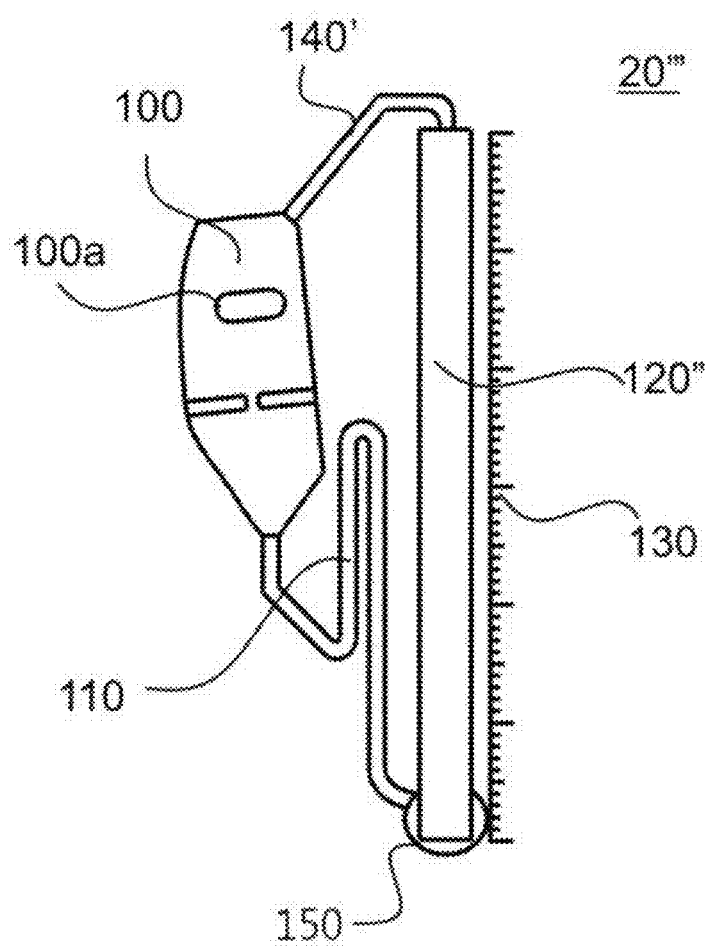

[FIG. 3A]
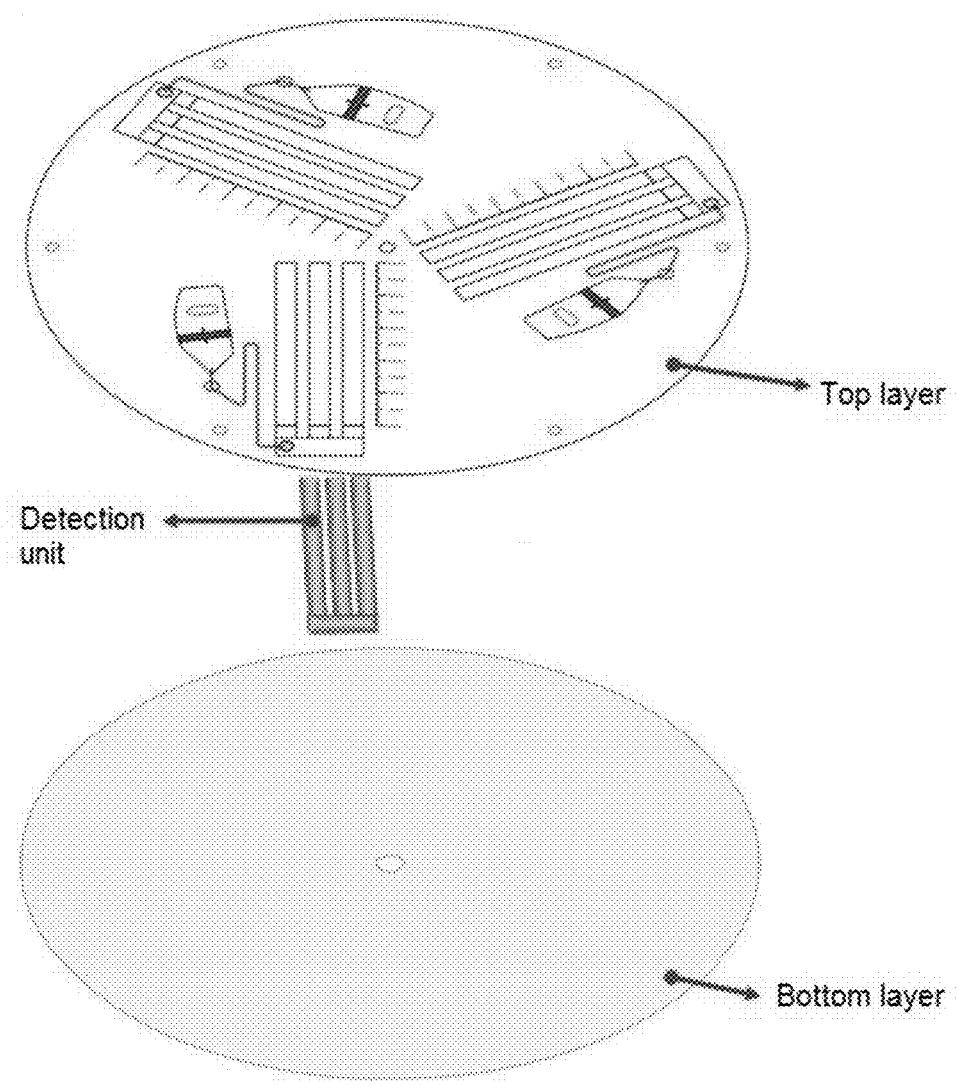

[FIG. 3B]
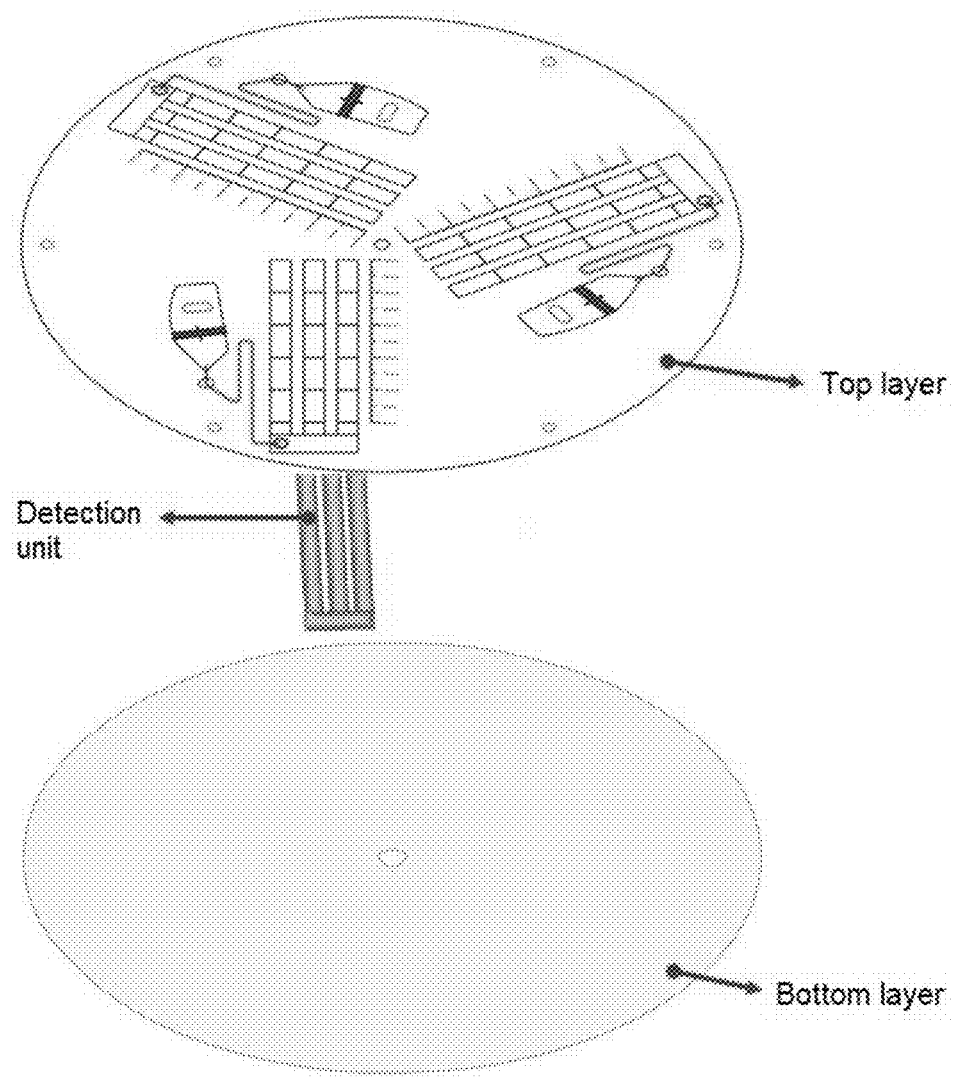

[FIG. 3C]
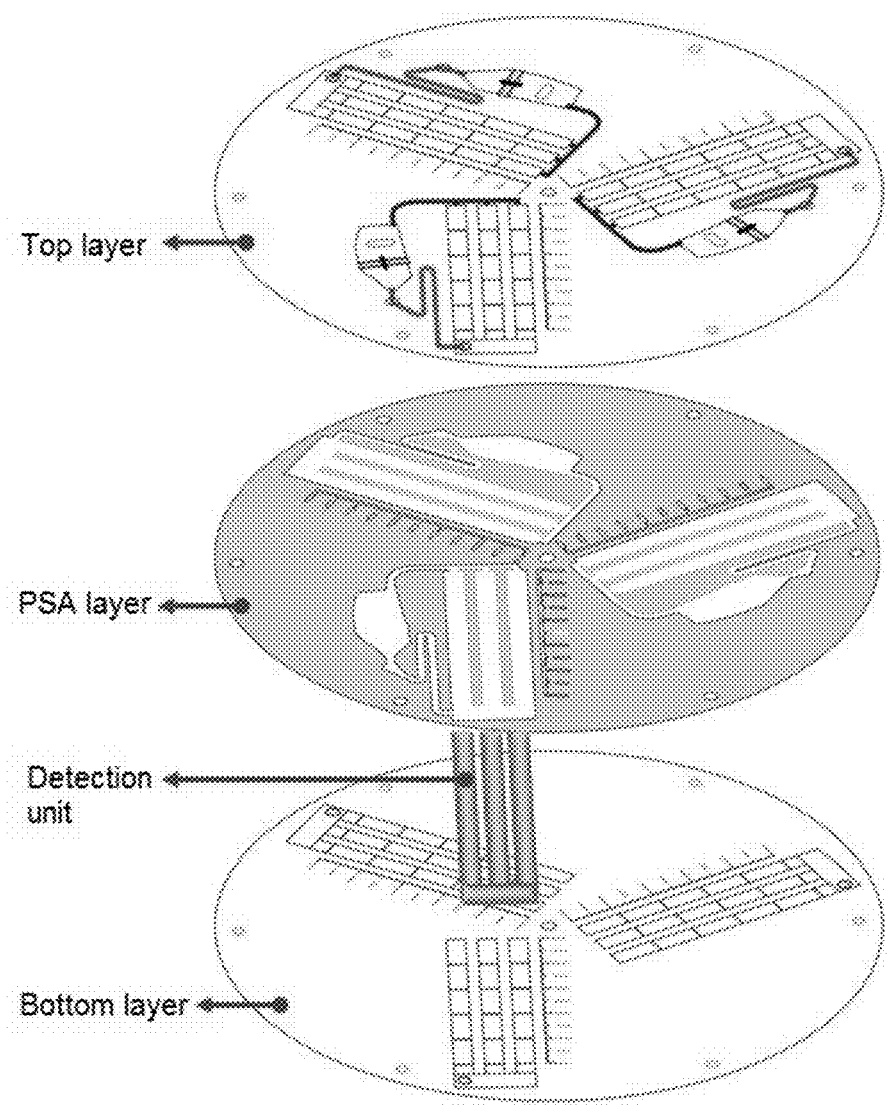

[FIG. 4A]
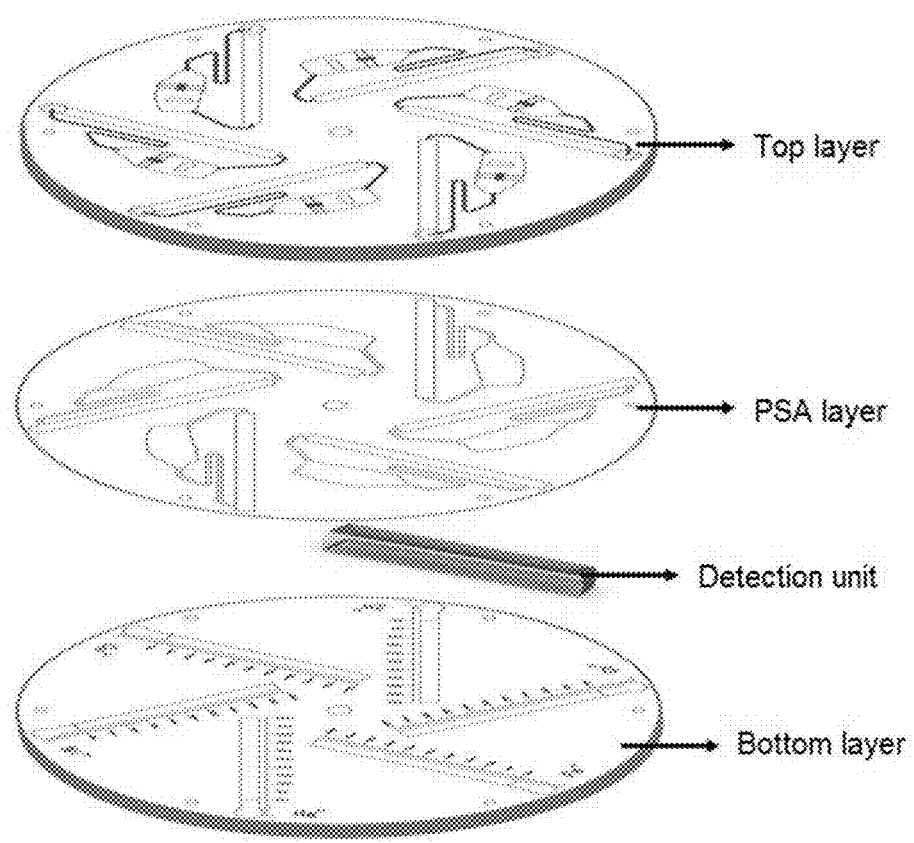

[FIG. 4B]
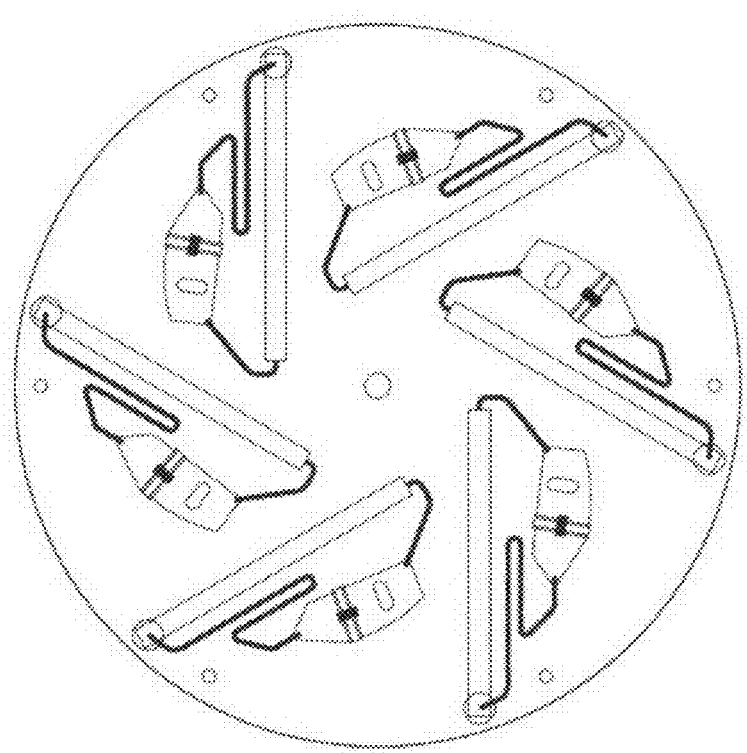

[FIG. 4C]
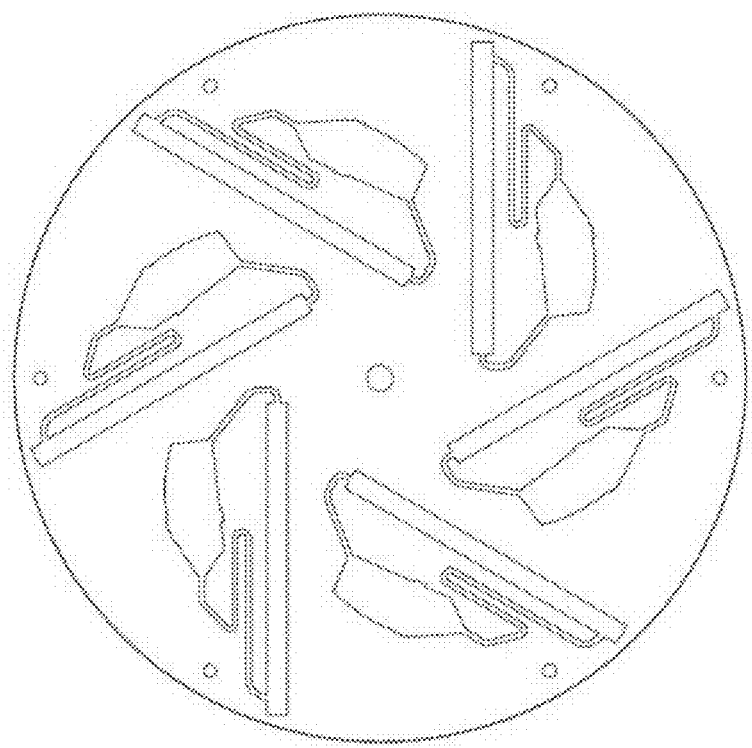

[FIG. 4D]
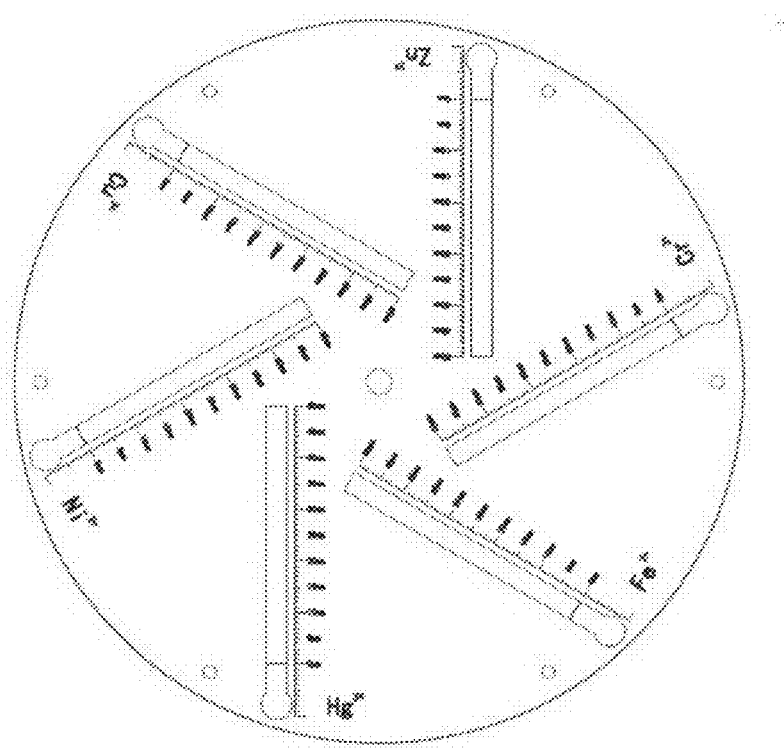

[FIG. 5]
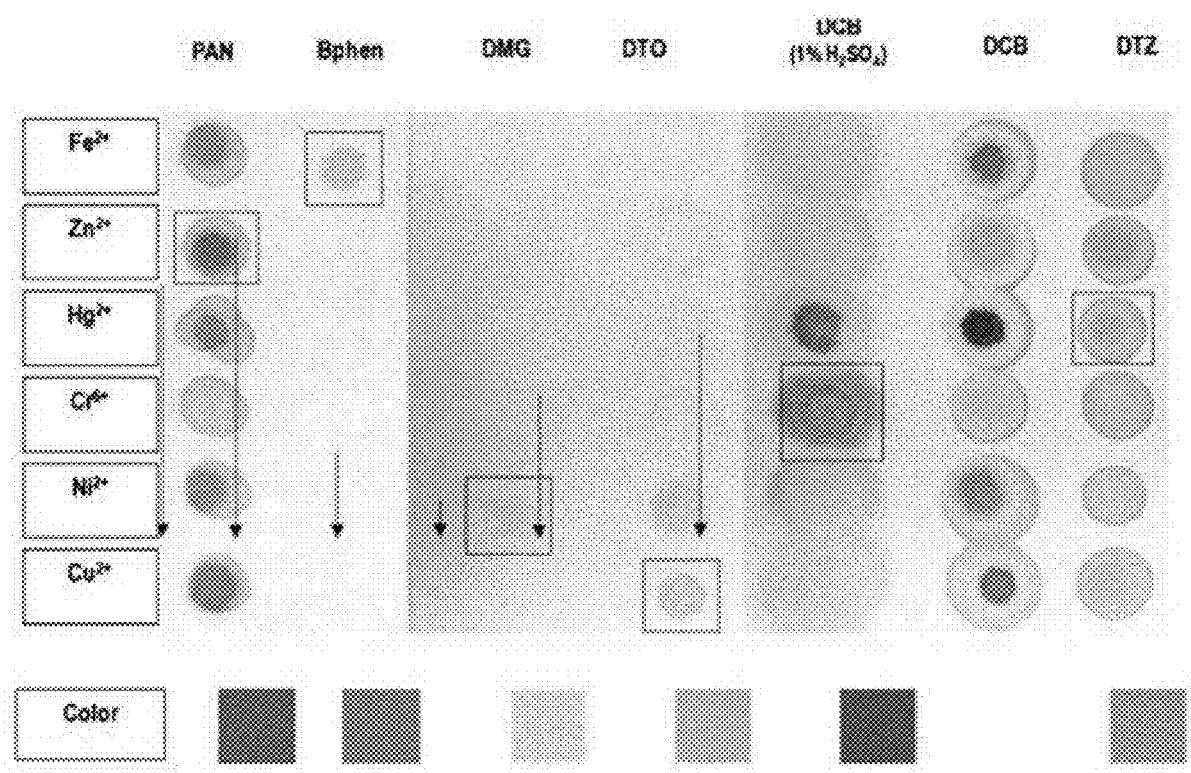

[FIG. 6]
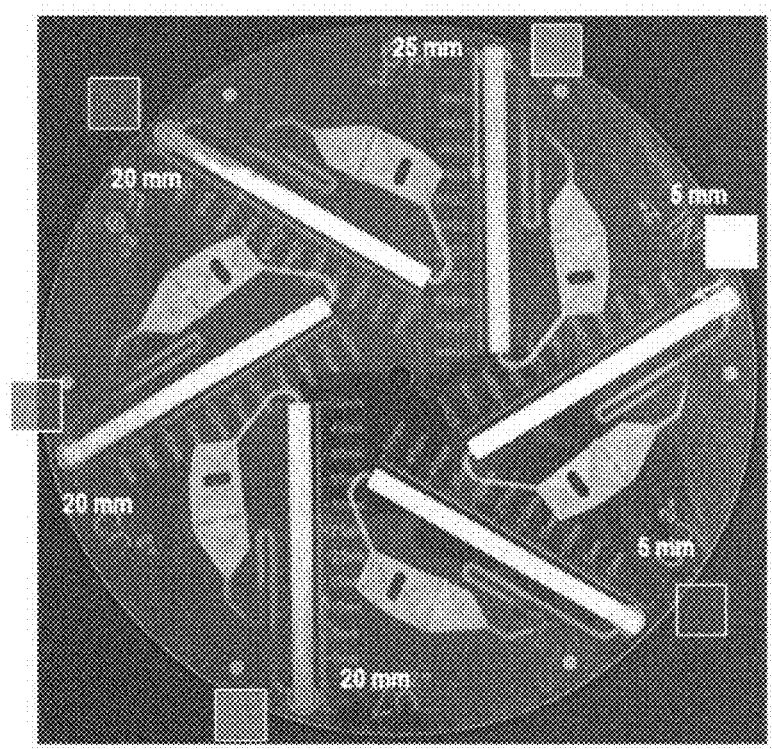

[FIG. 7A]
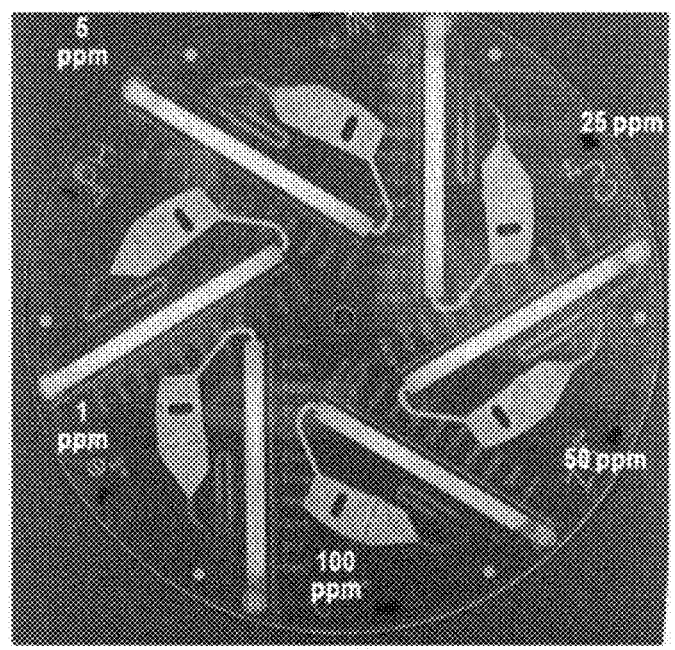
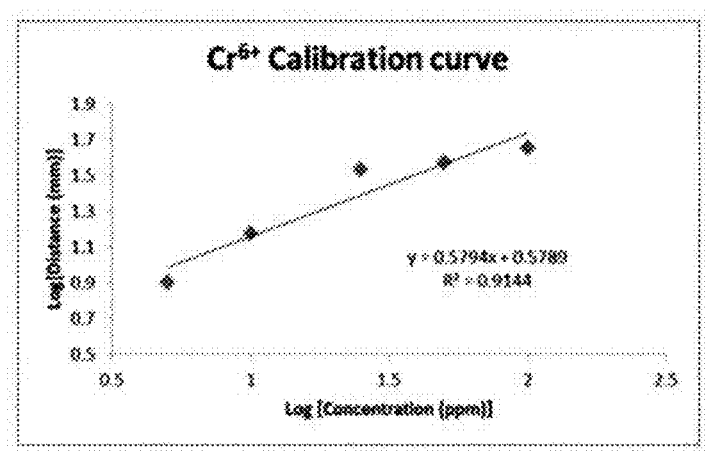

[FIG. 7B]
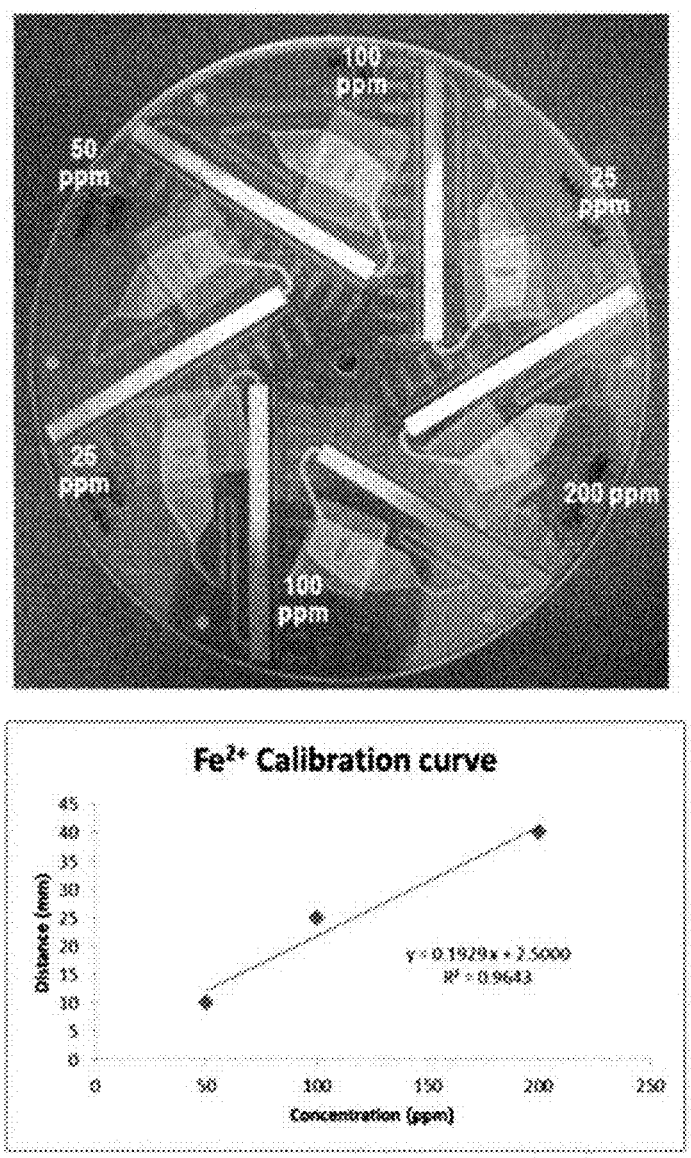

[FIG. 8]
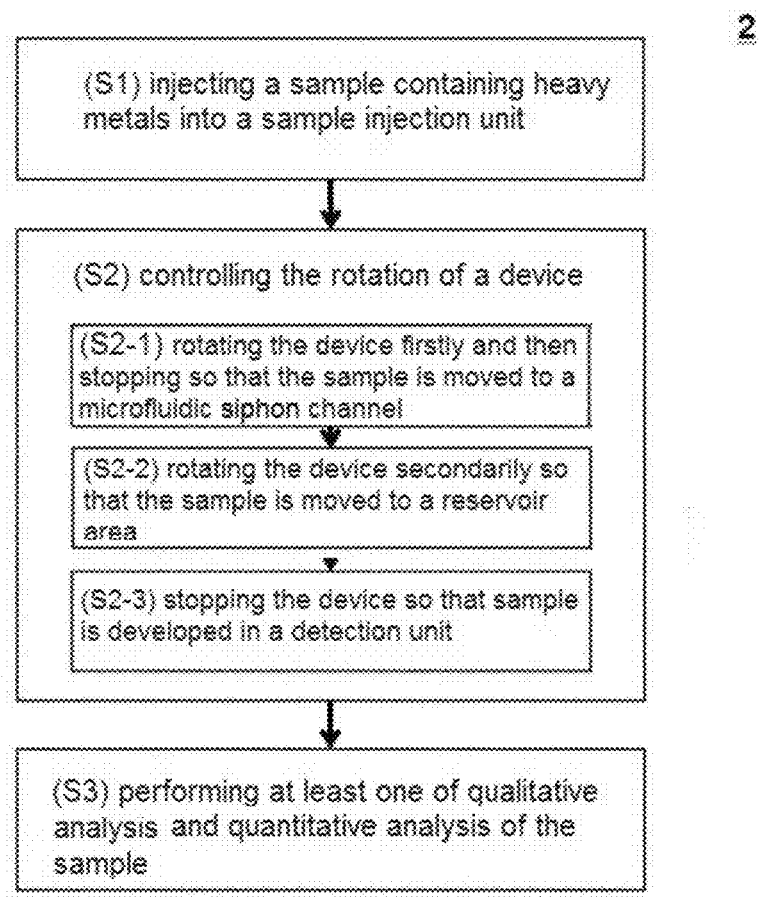

[FIG. 9]
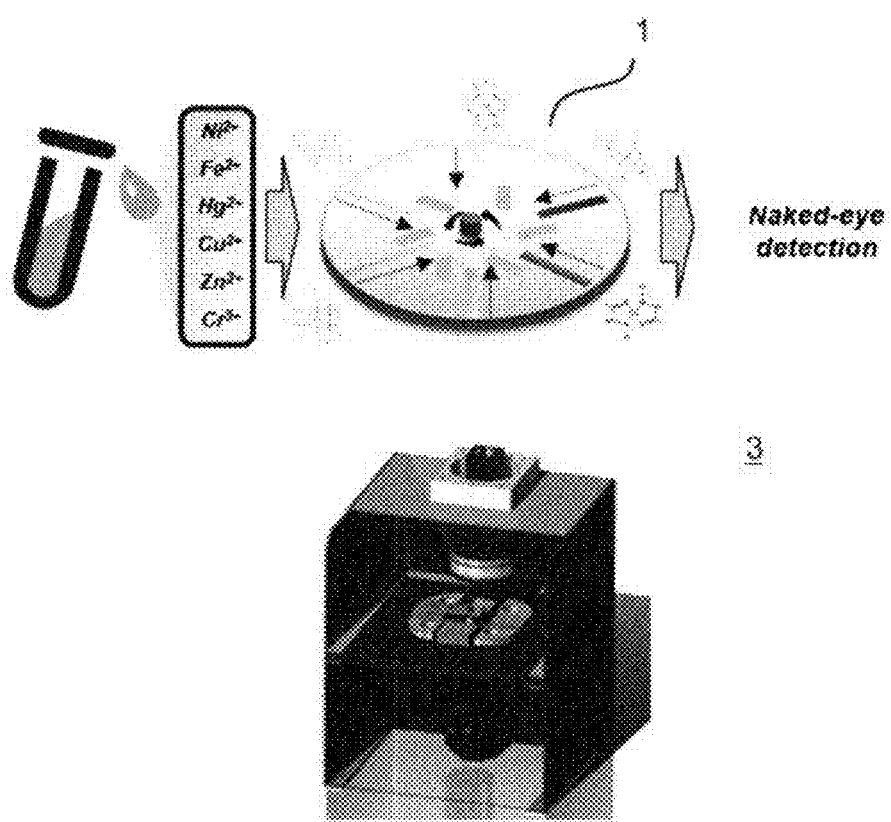

DEVICE AND METHOD FOR QUALITATIVE AND QUANTITATIVE ANALYSIS OF HEAVY METALS UTILIZING ROTARY DISC SYSTEM

CROSS-REFERENCE TO RELATED APPLICATIONS

This application is a national phase entry under 35 U.S.C. § 371 of International Patent Application No. PCT/KR2018/012738, filed on Oct. 25, 2018, published in Korean, which claims priority from Korean Patent Application No. 10-2017-0154395, filed on Nov. 20, 2017, and Korean Patent Application No. 10-2018-0053639, filed on May 10, 2018, the disclosures of which are hereby incorporated herein by reference.

BACKGROUND OF THE INVENTION

Field of the Invention

The present invention relates to a device and a method for qualitative analysis and quantitative analysis of heavy metals and, more particularly, to a device and a method for qualitative analysis and quantitative analysis of heavy metals using a rotatable disk system.

Description of the Related Art

In general, the most widely used method for detecting heavy metals is spectroscopic analysis such as inductively coupled plasma mass spectrometry or atomic absorption/emission spectrometry. Mass spectrometry and spectroscopy based heavy metal detection methods are accurate and have high detection limits, but they are expensive and require skilled analytical techniques, making it difficult to perform a heavy metal analysis in the field quickly and simply.

It is required to develop economical and cost-effective color development based heavy metal analysis system for replacing expensive mass spectrometry and spectroscopy based heavy metal analysis equipment, and development of miniaturized analysis system that can be conveniently applied in the field is required. In addition, it is required to develop a system capable of qualitative analysis as well as qualitative analysis of heavy metals while shortening analysis time by performing simultaneous detection of multiple heavy metals.

In addition, in the case where a plurality of heavy metals exist in one fluid sample, it is required to implement a method for performing the analysis more easily and quickly In addition, when a fluid sample containing heavy metals is developed in a detection unit and quantitative analysis is performed according to a development distance, a method for performing a more accurate quantitative analysis is required. Further, there is a need for a method for performing the movement of the fluid sample more uniformly when the fluid sample is developed in the detection unit and preventing the moisture condensation phenomenon in the detection unit.

SUMMARY OF THE INVENTION

The present invention pertains to a device for qualitative analysis and quantitative analysis comprising a rotatable platform and a plurality of microfluidic structures disposed radially and symmetrically on the rotatable platform. Each of the plurality of the microfluidic structures comprises a sample injection unit into which a fluid sample containing heavy metals is injected; a microfluidic channel (a siphon channel) which is a passage through which the sample can be moved to a detection unit and connects the sample injection unit to the one end of the detection unit; the detection unit comprising a plurality of detection members, which is coated with an organic substance capable of causing the color development reaction with the heavy metals of the sample; and a ruler for measuring the color developed distance. Each of the plurality of the microfluidic structures may receive different kinds of samples. The rotation of the device is controlled so that the sample moves from the sample injection unit to the microfluidic channel and then to the detection unit, and the qualitative analysis through the color development reaction of the heavy metals in the detection unit and the quantitative analysis through the measurement of the color developed distance may be possible.

Further, in the device for qualitative analysis and quantitative analysis according to the present invention, each of the plurality of the detection members may be coated with respective different reagents.

Further, in the device for qualitative analysis and quantitative analysis according to the present invention, each of the plurality of the detection members may comprise a plurality of sections coated with organic ligands of respective different concentrations.

Further, in the device for qualitative analysis and quantitative analysis according to the present invention, the detection unit may comprise a reservoir area which connects each one end of the plurality of the detection members with the microfluidic channel.

Further, in the device for qualitative analysis and quantitative analysis according to the present invention, each of the detection members comprises a plurality of sections coated with organic ligands of respective different concentrations, and the concentration of the organic ligand coated in the section located i-th from the reservoir area may be lower than the concentration of the organic ligand coated in the section located i-1-th from the reservoir area, wherein i may be a natural number from 1 to n.

Further, the device for qualitative analysis and quantitative analysis according to the present invention further comprises an air circulation channel connecting between the sample injection unit and the other end of the detection unit, wherein the air circulation channel can increase the rate of evaporation of the fluid sample in the detection unit and prevent moisture condensation phenomenon in the detection unit.

Further, in the device for qualitative analysis and quantitative analysis according to the present invention, the sample injection unit may include a space capable of receiving the sample and an opening through which the sample can be injected.

Further, in the device for qualitative analysis and quantitative analysis according to the present invention, the control of the rotation of the device can be accomplished by rotating the device firstly and then stopping so that the sample injected into the sample injection unit is moved to the microfluidic channel; rotating the device secondarily so that the sample moved to the microfluidic channel is moved to the reservoir area; and stopping the device so that the sample moved to the reservoir area is developed in the detection unit.

Further, in the device for qualitative analysis and quantitative analysis according to the present invention, the microfluidic channel may include a portion of a "U" shaped tube so that the sample can be received within the microfluidic channel after the first rotation and before the second rotation of the device.

Also, in the device for qualitative analysis and quantitative analysis according to the present invention, the first rotation may be performed at 2000 to less than 4000 RPM for 5 to 2.0 seconds and the second rotation may be performed at 4000 to 6000 RPM for 3 to 10 seconds.

Further, in the device for qualitative analysis and quantitative analysis according to the present invention, the rotatable platform is a circular disk and may have a diameter of 12 cm to 20 cm.

Further, in the device for qualitative analysis and quantitative analysis according to the, present invention, the heavy metals that may be included in the sample may comprise $Fe^{2+}$, $Zn^{2+}$, $Hg^{2+}$, $Cr^{6+}$, $Ni^{2+}$, or $Cu^{2+}$.

Further, in the device for qualitative analysis and quantitative analysis according to the present invention, the organic material previously applied to the detection unit may comprise any one selected from the group consisting of dimethylglyoxime, bathophenanthroline, dithiooxamide, dithizone, diphenylcarbazide and 1-(2-pyridylazo)-2-naphthol.

Further, the present invention pertains to an analytic method of a fluid sample containing heavy metals by using the qualitative analysis and quantitative analysis device according to the present ion. The analytic method comprises: (S1) injecting the sample into the sample injection unit; (S2) controlling the rotation of the device; and (S3) performing at least one of qualitative analysis and quantitative analysis of the sample developed in the detection unit.

Further, in the analytic method of a fluid sample containing heavy metals according to the present invention, the injection of the sample into the sample injection unit of the step (S1) may comprise injecting the fluid sample containing different kinds of the heavy metals into each of the plurality of the microfluidic structures, or injecting the fluid sample containing same kinds of the heavy metals of varying concentrations into each of the plurality of the micro fluidic structures.

Further, in the analytic method of a fluid sample containing heavy metals according to the present invention, the controlling of the rotation of the device of the step (S2) may comprise (S2-1) rotating the device firstly and then stopping so that the sample injected into the sample injection unit is moved to the microfluidic channel; (S2-2) rotating the device secondarily so that the sample moved to the microfluidic channel is moved to the reservoir area; and (S2-3) stopping the rotation of the device so that the sample moved to the reservoir area is developed in the detection unit.

Further, in the analytic method of a fluid sample containing heavy metals according to the present invention, the performance of at least one of qualitative analysis and quantitative analysis of the sample of the step (S3) may comprise performing at least one of (S3-1) qualitative analysis through the color development reaction of the sample developed in the detection unit and (S3-2) quantitative analysis through the measurement of the color developed distance.

EFFECT OF THE INVENTION

According to the device for qualitative analysis and quantitative analysis and the analysis method of the sample using the same according to one embodiment of the present invention, the increase of the detection limit of heavy metals through the control of the automated fluidic control and the control of the torque and capillary force is possible. It is possible to improve the detection limit of heavy metal ions by the torque control. That is, it is possible to improve the detection limit by controlling the color development reaction time and the colored area via adjustment of the centrifugal force and the capillary force by control of the rotation of the device.

According to the device for qualitative analysis and quantitative analysis and the analysis method of the sample using the same according to one embodiment of the present invention, qualitative analysis and quantitative analysis of several heavy metals can be performed with one device. According to the present invention, economical and rapid multi-metal qualitative/quantitative analysis is possible. It is more economical than conventional expensive spectroscopy or mass spectrometry based heavy metal detector and can shorten analysis time. In addition, the configurations for qualitative analysis and quantitative analysis can be integrated into one miniaturized device, and can be applied quickly and conveniently in the field where qualitative/quantitative analysis of heavy metals is required.

In addition, since the channel (a microfluidic channel) and the detection unit are all patterned in one device, the fabrication of the device for qualitative analysis and quantitative analysts is simple.

In addition, in the device for qualitative analysis and quantitative analysis according to the present invention, even when multiple heavy metals are present in one fluid sample, the analysis can be performed more simply and quickly In addition, it is possible to improve the accuracy of the measurement even in the quantitative analysis of heavy metals contained in the fluid sample, by coating each of the detection members with organic ligands with a concentration gradient in place of coating with the same concentration of the organic ligands throughout each of the detection members.

Further, according to the device for qualitative analysis and quantitative analysis and the analysis method of the sample using the qualitative analysis and quantitative analysis device according to one embodiment of the present invention, the air circulation channel is provided so that the moisture condensation in the detection unit can be prevented when the fluid sample is developed in the detection unit and the reservoir area is provided at the end of the microfluidic channel so that one end of the detection unit is located in the reservoir area, and thus the fluid sample can move more uniformly when the fluid sample is developed in the detection unit.

BRIEF DESCRIPTION OF THE DRAWINGS

FIG. 1A shows a device for qualitative analysis and quantitative analysis according to one embodiment of the present invention, and FIGS. 1B and 1C show microfluidic structures of the device for qualitative analysis and quantitative analysis of FIG. 1A.

FIG. 1D shows a device for qualitative analysis and quantitative analysis according to another embodiment of the present invention, and FIGS. 1E and 1F show microfluidic structures of the device for qualitative analysis and quantitative analysis of FIG. 1D.

FIG. 1G shows a device for qualitative analysis and quantitative analysis according to another embodiment of the present invention, and FIGS. 1H and 1I show microfluidic structures of the device for qualitative analysis and quantitative analysis of FIG. 1G.

FIG. 2A illustrates a device for qualitative analysis and quantitative analysis according to another embodiment of the present invention, and FIG. 2B shows microfluidic structures of the device for qualitative analysis and quantitative analysis of FIG. 2A.

FIGS. 3A to 3C show each layer of a rotatable platform comprising microfluidic structures of the device for qualitative analysis and quantitative analysis according to FIGS. 1A, 1D and 1G, respectively.

FIGS. 4A to 4D show each layer of a rotatable platform comprising microfluidic structures of the device for qualitative analysis and quantitative analysis according to FIG. 2A.

FIG. 5 shows an example of a color development reaction between heavy metal ions and organic complexing agents.

FIG. 6 shows an example of simultaneous qualitative analysis of heavy metals using the device for qualitative analysis and quantitative analysis according to the present invention.

FIGS. 7A and 7B show examples of quantitative analysis of heavy metals using the device for qualitative analysis and quantitative analysis according to the present invention.

FIG. 8 shows a flowchart of a method of analyzing a sample using the device for qualitative analysis and quantitative analysis according to the present invention.

FIG. 9 shows a system for qualitative analysis and quantitative analysis that includes and can rotate the device for qualitative analysis and quantitative analysis according to the present invention.

DETAILED DESCRIPTION OF THE INVENTION

In the device for qualitative analysis and quantitative analysis comprising a rotatable platform and a plurality of microfluidic structures disposed radially and symmetrically on the rotatable platform according to present invention, each of the plurality of the microfluidic structures comprises a sample injection unit into which a fluid sample containing heavy metals is injected; a microfluidic channel which is a passage through which the sample can be moved to a detection unit and connects the sample injection unit to the one end of the detection unit; the detection unit comprising a plurality of detection members, which is coated with an organic substance capable of causing the color development reaction with the heavy metals of the sample; and a ruler for measuring the color developed distance. Each of the plurality of the microfluidic structures may receive different kinds of samples. The rotation of the device is controlled so that the sample moves from the sample injection unit to the microfluidic channel and then to the detection unit, and the qualitative analysis through the color development reaction of the heavy metals in the detection unit and the quantitative analysis through the measurement of the color developed distance may be possible.

Further, in the device for qualitative analysis and quantitative analysis according to the present invention, each of the plurality of detection members may be coated with respective different reagents.

Further, in the device for qualitative analysis and quantitative analysis according to the present invention, each of the detection members may comprise a plurality of sections coated with organic ligands of respective different concentrations.

Further, in the device for qualitative analysis and quantitative analysis according to the present invention, the detection unit may comprise a reservoir area which connects each one end of the plurality of detection members with the microfluidic channel.

Further, in the device for qualitative analysis and quantitative analysis according to the present invention, the development area comprises a plurality of sections coated with organic ligands of respective different concentrations, and the concentration of the organic ligand coated in the section located i-th from the reservoir area may be lower than the concentration of the organic ligand coated in the section located i-1-th from the reservoir area, wherein i may be a natural number from 1 to n. Further, the device for qualitative analysis and quantitative analysis according to the present invention further comprises an air circulation channel connecting between the sample injection unit and the other end of the detection unit, wherein the air circulation channel can increase the rate of evaporation of the fluid sample in the detection unit and prevent moisture condensation phenomenon in the detection unit.

Further, in the device for qualitative analysis and quantitative analysis according to the pr sen invention, the sample injection unit may include a space capable of receiving the sample and an opening through which the sample can be injected.

Further, in the device for qualitative analysis and quantitative analysis according to the present invention, the control of the rotation of the device can be accomplished by rotating the device firstly and then stopping so that the sample injected into the sample injection unit is moved to the microfluidic channel; rotating the device secondarily so that the sample moved to the microfluidic channel is moved to the reservoir area; and stopping the device so that sample moved to the reservoir area is developed in the detection unit.

Further, in the device for qualitative analysis and quantitative analysis according to the present invention, the microfluidic channel may include a portion of a "U" shaped tube so that the sample can be received within the microfluidic channel after the first rotation and before the second rotation of the device.

Also, in the device for qualitative analysis and quantitative analysis according to the present invention, the first rotation may be, performed at 2000 to 4000 RPM for 5 to 20 seconds and the second rotation may be performed at 4000 to 6000 RPM for to 10 seconds.

Further, in the device for qualitative analysis and quantitative analysis according to the present invention, the rotatable platform is a circular disk and may have a diameter of 12 cm to 20 cm.

Further, in the device for qualitative analysis and quantitative analysis according to the present invention, the heavy metals that may be included in the sample may comprise $Fe^{2+}$, $Zn^{2+}$, $Cr^{6+}$, $Ni^{2+}$, or $Cu^{2+}$.

Further, in the device for qualitative analysis and quantitative analysis according to the present invention, the organic material previously applied to the detection unit may comprise any one selected from the group consisting of dimethylglyoxime, bathophenanthroline, dithiooxamide, dithizone, diphenylcarbazide and 1-(2-pyridylazo)-2-naphthol.

Further, in the analytic method of a fluid sample containing heavy metals by using the qualitative analysis and quantitative analysis device according to the present invention, the method comprises: (S1) injecting the sample into the sample injection unit; (S2) controlling the rotation of the device; and (S3) performing at least one of qualitative analysis and quantitative analysis of the sample developed in the detection unit.

Further, in the analytic method of a fluid sample containing heavy metals according to the present invention, the injection of the sample into the sample injection unit of the step (S1) may comprise injecting the fluid sample containing different kinds of the heavy metals into each of the plurality of the microfluidic structures, or injecting the fluid sample containing same kinds of the heavy metals of varying concentrations into each of the plurality of the microfluidic structures.

Further, in the analytic method of a fluid sample containing heavy metals according to the present invention, the controlling of the rotation of the device of the step (S2) may comprise (S2-1) rotating the device firstly and then stopping so that the sample injected into the sample injection unit is moved to the microfluidic channel; (S2-2) rotating the device secondarily so that the sample moved to the microfluidic channel is moved to the reservoir area; and (S2-3) stopping the rotation of the device so that the sample moved to the reservoir area is developed in the detection unit. Further, in the analytic method of a fluid sample containing heavy metals according to the present invention, the performance of at least one of qualitative analysis and quantitative analysis of the sample of the step (S3) may comprise performing at least one of (S3-1) qualitative analysis through the color development reaction of the sample developed in the detection unit and (S3-2) quantitative analysis through the measurement of the color developed distance.

Hereinafter, the device and the method for qualitative analysis and quantitative analysis of heavy metals using a rotatable disk system according to the present invention will be described in detail. The accompanying drawings, which are included to provide a further understanding of the invention, illustrate embodiments of the present invention and the technical scope of the present invention is not limited thereto.

In addition, the same or corresponding components are denoted by the same reference numbers regardless of the figures, and redundant description thereof krill be omitted. For convenience of explanation, the size and shape of each constituent member shown may be exaggerated or reduced.

FIG. 1A shows a device for qualitative analysis and quantitative analysis (1) according to one embodiment of the present invention, and FIG. 1B shows microfluidic structures (20) of the rotatable disk system of FIG. 1A.

First, referring FIG. 1A, the device for qualitative analysis and quantitative analysis (1) includes the rotatable platform (10) and a plurality of the microfluidic structures (20) provided on the rotatable platform (10). The rotatable platform (10) may be, for example, a circular disk, and the size may be, for example, in one embodiment 12 cm to 20 cm in diameter, and in another embodiment, less than 12 cm in diameter.

The rotatable platform (10) includes the plurality of the microfluidic structures (20) which positioned radially and symmetrically on the rotatable platform (10). For example, the plurality of the microfluidic structures (20) may comprise two, three, four, six, eight, ten, or twelve of the structures. In FIG. 1A, three microfluidic structures (20) are shown disposed on the rotatable platform (10).

Referring to FIG. 1B, each microfluidic structure (20) of the plurality of the microfluidic structures (20) is shown. The microfluidic structures (20) include a top layer (see FIG. 3A), a detection unit (120) coated with an organic substance capable of causing a color development reaction with the heavy metals in a fluid sample, and a bottom layer (see FIG. 3A). The top layer includes a sample injection unit (100) into which a fluid sample containing the heavy metals is injected, a microfluidic channel (110) through which the fluid sample can move to the detection unit, a portion where the detection unit (120) can be inserted, and a ruler (130) for measuring the color developed distance. The bottom layer is a pressure-sensitive adhesive layer which is not patterned.

Each microfluidic structure (20) of the plurality of the microfluidic structures (20) may receive the fluid sample containing different kinds of the heavy metals. The heavy metals that may be included in the fluid sample may include, for example, $Fe^{2+}$, $Zn^{2+}$, $Hg^{2+}$, $Cr^{6+}$, $Ni^{2+}$, $Cu^{2+}$, etc.

The sample injection unit (100) includes a space for accommodating a fluid sample containing the heavy metals and an opening (100a) through which the fluid sample can be injected into the space. The sample injection unit (100) and one end of the detection unit (120) may be connected to the microfluidic channel (110). Further, the sample injection unit (100) may include a blocking unit (100b) which prevents the sample injected through the opening (100a) from flowing directly into the microfluidic channel (110) and stores the sample in the inner space of the sample injection unit (100) by using drop of the channel. Since the vicinity of the rear end portion (100c) of the sample injection unit (100) where the microfluidic channel (110) is connected to the sample injection unit (100) has, for example, a streamlined shape, when the fluid sample injected into the injection unit (100) moves to the microfluidic channel (110), the resistance of the fluid sample is minimized and all of the fluid sample injected into the sample injection unit (100) is moved to the microfluidic channel (110).

The microfluidic channel (110) may have a width of 1 min and a depth of 100 μm. The microfluidic channel (110) may comprise, for example, a portion of a "U" shaped tube. As will be described below, the fluid sample including the heavy metals after the first rotation and before the second rotation of the device for qualitative analysis and quantitative analysis (1) can move along the channel which is a passage through which the fluid sample moves due to the hydrophilicity of the microfluidic channel (110), and as a result, the fluid sample can be accommodated in the microfluidic channel (110).

The detection unit (120) may be made of a porous hydrophilic material, for example, paper, nitrocellulose, cotton, silica based sol-gel matrix, etc., and may be preferably made of paper.

Meanwhile, the detection unit (120) comprises a plurality of the detection members (121, 122, 123). Although FIGS. 1A and 1B show one detection unit (120) comprising three detection members (121, 122, 123), the present invention is not limited thereto and the number of the detection members may be adjusted according to various environments in which the present invention is implemented. Each of the plurality of the detection members (121, 122, 123) of the detection unit (120) may be coated with different reagents. These pre-applied reagents each contain a specific organic material (organic ligand) that can cause a color development reaction with the heavy metals in the fluid sample (see FIG. 5 and Table 1). Therefore, when one organic sample injected into the sample injection unit (100) includes a plurality of the heavy metals, the plurality of the heavy metals may be detected in each of the plurality of the detection members (121, 122, 123) coated with each of the different reagents. For example, PAN (1-(2-pyridylazo)-2-naphthol) for detecting $Zn^{2+}$ may be coated in the detection member (121), Bphen (bathophenanthroline) for detecting $Fe^{2+}$ may be coated in the detection member (122), and DMG (dimethylglyoxime) for detecting $Ni^{2+}$ may be coated in the detection member (123).

Also, the detection unit (120) comprises a reservoir area (124) connecting the microfluidic channel (110) to the plurality of the detection members (121, 122, 123). The reservoir area (124) may or may not be coated with an organic material. The reservoir area (124) is connected to each one end of the plurality of the detection members (121, 122, 123). Further, the microfluidic channel (110) is connected to the reservoir area (124). The fluid sample moved from the sample injection unit (100) to the microfluidic channel (110) during the first rotation of the rotatable platform (10) is moved from the microfluidic channel (110) to the reservoir area (124) of the detection unit (120) connected to the microfluidic channel (110) during the secondary rotation of the rotatable platform (10). At this time, the fluid sample remains in the reservoir area (124) without being developed into the plurality of the detection members (121, 122, 123) of the detection unit (120) by the centrifugal force due to the rotation. When the secondary rotation of the rotatable platform (10) is stopped, the fluid sample is developed from the reservoir area (124) to each of the plurality of the detection members (121, 122, 123). A more detailed description thereof will be given below with reference to FIG. 8.

The ruler (130) is positioned alongside of the detection unit (120) in the vicinity of the detection unit (120). The ruler (130) may be, for example, scaled in millimeters (mm). Alternatively, it may be scaled in units of concentration such as ppm, ppb, etc., in addition to the length unit such as mm in the scale unit (130). In the case where the scale is expressed in terms of the concentration unit in the ruler (130), it may be expressed in terms of a concentration unit obtained by substituting the development distance of the relevant heavy metals into a calibration curve (see FIGS. 6A and 6B).

FIG. 1C shows exemplary dimensions of the microfluidic structures (20) of the rotatable disk system of FIG. 1B. Exemplary dimensions of the microfluidic structures (20) are not limited to those shown in FIG. 1C, but may be modified or changed according to various environments embodied in the present invention.

FIG. 1D shows a device for qualitative analysis and quantitative analysis (1') according to another embodiment of the present invention, and FIG. 1E shows the microfluidic structures (20') of the rotatable disk system of FIG. 1D.

Each of the plurality of the detection members (121', 122', 123') of the detection unit (120') is not coated with the organic ligands of the same concentration but coated with organic ligands of different concentrations by providing a concentration gradient in a plurality of (n, where n is a natural number of 2 or more) sections of the detection members (121', 122', 123') as shown in FIG. 1E. The number n of sections may be, for example, 2 or more and 10 or less, or 5 or 6, for example. More specifically, upon checking the detection member (121'), the first section ($121'_1$) closest to the reservoir area (124) is coated with the highest concentration of the organic ligand, and the next adjacent second section ($121'_2$) is coated with a lower concentration than that of the organic ligand coated in the first section ($121'_1$). The next third section ($121'_3$) is coated with a lower concentration than that of the organic ligand coated in the second section ($121'_2$), and the subsequent sections are also coated with increasingly lower concentrations of the organic ligands. And the n-th section ($121'_n$) farthest from the reservoir area (124) is coated with the lowest concentration of the organic ligand. That is, the concentration of the organic ligand coated in the i-th section ($121'_i$) from the reservoir area (124) is lower than that of the organic ligand coated in the (i-1)-th section ($121'_{i-1}$). Here, i is a natural number from 1 to n.

The amount of the fluid sample developed from the n-th section ($121'_n$) farthest to the reservoir area (124) toward the first section ($121'_1$) closest to the reservoir area (124) increases. According to the present invention, the concentration of the coated organic ligand is increased toward the first section ($121'_1$) closest to the reservoir area (124) from the n-th section ($121'_n$) farthest from the reservoir area (124). It is possible to prevent the speed at which the fluid sample is developed at the detection member (121') from being increased faster than the rate at which the organic ligand coated on the detection member (121') reacts with the heavy metals in the fluid sample (color development reaction) so that in the analysis of the heavy metals in the fluid sample, the accuracy of the measurement can be further increased. On the other hand, the detection member (122') and the detection member (123') are also coated with organic ligands with the concentration gradient in the above-described manner with respect to the detection member (121').

For example, when in order to detect $Zn^{2+}$, PAN (1-(2-pyridylazo)-2-naphthol) as an organic substance is coated on one of the detection members (121', 122', 123') (for example, the detection member (121')). When the number of sections of the detection member is 5, the concentration of the organic ligand coated on each of the first section ($121'_1$), the second section ($121'_2$), the third section ($121'_3$), the fourth section ($121'_4$) and the fifth section ($121'_5$) is 50, 35, 20, 5 and 1 mM, respectively.

Also, for example, when in order to detect $Fe^{2+}$, Bphen (bathophenanthroline) as an organic substance is coated on one of the detection members (121', 122', 123') (for example, the detection member (121')). When the number of sections of the detection member is 5, the concentration of the organic ligand coated on each of the first section ($121'_1$), the second section ($121'_2$), the third section ($121'_3$), the fourth section ($121'_4$) and the fifth section ($121'_5$) is 10, 5, 1, 0.5 and 0.1 mM, respectively.

Further, for example, when in order to detect $Ni^{2+}$, DMG (dimethylglyoxime) as an organic substance is coated on one of the detection members (121', 122', 123') (for example, the detection member (121')). When the number of sections of the detection member is 5, the concentration of the organic ligand coated on each of the first section ($121'_1$), the second section ($121'_2$), the third section ($121'_3$), the fourth section ($121'_4$) and the fifth section ($121'_5$) is 50, 10, 5, 1 and 0.5 mM, respectively.

Also, for example, when in order to detect $Cu^{2+}$, DTO (dithiooxamide) as an organic substance is coated on one of the detection members (121', 122', 123') (for example, the detection member (121')). When the number of sections of the detection member is 5, the concentration of the organic ligand coated on each of the first section ($121'_1$), the second section ($121'_2$), the third section ($121'_3$), the fourth section ($121'_4$) and the fifth section ($121'_5$) is 10, 8, 6, 4 and 2 mM, respectively.

Further, for example, when in order to detect $Cr^{6+}$, DCB (diphenylcarbazide) supplemented with 1% $H_2SO_4$ as an organic substance is coated on one of the detection members (121', 122', 123') (for example, the detection member (121')). When the number of sections of the detection member is 5, the concentration of the organic ligand coated on each of the first section ($121'_1$), the second section ($121'_2$), the third section ($121'_3$), the fourth section ($121'_4$) and the fifth section ($121'_5$) is 20, 10, 5, 2 and 1 mM, respectively.

Also, for example, when in order to detect $Hg^{2+}$, DTZ (dithizone) as an organic substance is coated on one of the detection members (121', 122', 123') (for example, the detection member (121')). When the number of sections of the detection member is 5, the concentration of the organic ligand coated on each of the first section ($121'_1$), the second section ($121'_2$), the third section ($121'_3$), the fourth section ($121'_4$) and the fifth section ($121'_5$) is 50, 25, 10, 5 and 1 mM, respectively.

FIG. 1F shows exemplary dimensions of the microfluidic structures (20') of the rotatable disk system of FIG. 1D. Exemplary dimensions of the microfluidic structures (20') are not limited to those shown in FIG. 1F, but may be modified or changed according to various environments embodied in the present invention.

FIG. 1G shows a device for qualitative analysis and quantitative analysis (1") according to another embodiment of the present invention, and FIG. 1H shows the microfluidic structures (20") of the rotatable disk system of FIG. 1G. The device for qualitative analysis and quantitative analysis (1") of FIG. 1H, like the device for qualitative analysis and quantitative analysis (1) of FIG. 1A, comprises the rotatable platform (10) and a plurality of the microfluidic structures (20") provided in and the rotatable platform (10). The top layer of the rotatable platform (10) includes the sample injection unit (100) into which a fluid sample containing the heavy metals is injected and the micro-fluidic channel (110) which is a passage through which the fluid sample can move to the detection unit. The portion of the top layer where the detection unit (120") is positioned may be variously modified and changed so that the detection unit (120") can be inserted, including a concave portion in conformity with the shape of the detection unit (120"). Also, the depth of the concave portion can be variously modified and changed according to the environment in which the present invention is actually implemented. The bottom layer includes a portion where the detection unit (120") can be inserted (see FIG. 3C) and a ruler (130) for measuring the color developed distance.

Meanwhile, the device for qualitative analysis and quantitative analysis (1") of FIG. 1G comprises an air circulation channel (140) unlike the device for qualitative analysis and quantitative analysis (1, 1') of FIGS. 1A and 1D. The air circulation channel (140) connects between the sample injection unit (100) and the other end of each of the plurality of the detection members (121', 122', 123') of the detection unit (120'). Due to this, the sample injection unit (100), the microfluidic channel (110), the detection unit (120'), the air circulation channel (140), and the sample injection unit (100) are connected to be circulated in order. By introducing the air circulation channel (140), the evaporation rate of the fluid sample of the detection unit (120') may be increased, and the moisture condensation phenomenon in the detection unit (120') may be prevented. On the other hand, with respect to the sample injection unit (100), since the air circulation channel (140) is located at the center of the circular disk-shaped rotatable platform (10) and the microfluidic channel (110) is positioned toward the edge of the rotatable platform (10), when the rotatable platform (10) rotates, the sample of the sample injection unit (100) moves to the microfluidic channel (110) by the centrifugal force and does not move to the air circulation channel (140). Additionally, in order to prevent the possibility of movement, a hole having a depth of about 1 mm and a diameter of about 0.8 mm is drilled at a point where the sample injection unit (100) and the air circulation channel (140) are connected to each other to form a capillary valve operated by an air pressure, thereby preventing the sample from moving from the sample injection unit (100) to the air circulating channel (140).

FIG. 1I shows exemplary dimensions of the microfluidic structures (20") of the rotatable disk system of FIG. 1G. Exemplary dimensions of the microfluidic structures (20") are not limited to those shown in FIG. 1I, but may be modified or changed according to various environments embodied in the present invention.

FIG. 2A illustrates a device for qualitative analysis and quantitative analysis (1'") according to another embodiment of the present invention, and FIG. 2B shows the microfluidic structures (20'") of the rotatable disk system of FIG. 2A. The device for qualitative analysis and quantitative analysis (1'") of FIG. 2A comprises, like the device for qualitative analysis and quantitative analysis (1) of FIG. 1A, the rotatable platform (10) and a plurality of the microfluidic structures (20'") provided in and the rotatable platform (10). The top layer of the rotatable platform (10) includes the sample injection unit (100) into which a fluid sample containing the heavy metals is injected and the microfluidic channel (110) which is a passage through which the fluid sample can move to the detection unit. The portion of the top layer where the detection unit (120'") is positioned may be variously modified and changed so that the detection unit (120'") can be inserted, including a concave portion in conformity with the shape of the detection unit (120'"). Also, the depth of the concave portion can be variously modified and changed according to the environment in which the present invention is actually implemented. The bottom layer includes a portion where the detection unit (120'") can be inserted (see FIG. 4D) and a ruler (130) for measuring the color developed distance.

The device for qualitative analysis and quantitative analysis (1'") of FIG. 2A comprises an air circulation channel (140') like the device for qualitative analysis and quantitative analysis (1") of FIG. 1G. The air circulation channel (140') connects between the sample injection unit (100) and the other end of the detection unit (120"). Due to this, the sample injection unit (100), the microfluidic channel (110), the detection unit (120"), the air circulation channel (140'), and the sample injection unit (100) are connected to be circulated in order.

Meanwhile, in the device for qualitative analysis and quantitative analysis (1'") of FIG. 2A, the detection unit (120") comprises one detection member. Further, the detection unit (120") does not have different concentrations of the organic ligands in each section unlike in the device for qualitative analysis and quantitative analysis (1, 1') of FIGS. 1D and 1G. Further, in the device for qualitative analysis and quantitative analysis (1'") of FIG. 2A, the entire detection unit (120") is coated with an organic material capable of causing the color development reaction with the heavy metals of the fluid sample so that the fluid sample can be developed and includes a reserve region (150) provided separately from the detection unit (120"). One end of the detection unit (120") is accommodated in the reservoir region (150). The reservoir region (150) is a recessed patterned area in each of the lower surface of the top layer and the upper surface of the bottom layer of the rotatable platform (10) of FIG. 4A so as to accommodate the fluid sample therein. The fluid sample accommodated in the microfluidic channel (110) during the first rotation of the rotatable platform (10) moves from the microfluidic channel (110) to the reservoir region (150) during the second rotation of the rotatable platform (10) and then is stored (i.e., trapped) in the reservoir area (150) without being developed into the detection unit (120") by the centrifugal force due to the rotation. When the second rotation of the rotatable platform (10) is stopped, the fluid sample is moved from the reservoir area (150) into the detection unit (120") where the fluid sample is developed. A more detailed description thereof will be given below with reference to FIG. 8.

In the description of the device for qualitative analysis and quantitative analysis (1''') of FIG. 2A and the microfluidic structures (20''') of FIG. 2B, the description of the components that overlap with those in the device for qualitative analysis and quantitative analysis (1, 1', 1") and the microfluidic structures (20, 20', 20") of FIGS. 1A to 1H refers to the descriptions of FIGS. 1A to 1H.

FIGS. 3A and 3B illustrate each layer of the rotatable platform (10) comprising the microfluidic structures (20, 20') of FIGS. 1A and 1D, respectively. The rotatable platform (10) including the microfluidic structures (20, 20') is mainly composed of two layers. In a top layer, the sample injection unit (100), the microfluidic channel (110), a space in which the detection unit (120, 120') can be inserted, and the ruler (130) are positioned. The thickness of the top layer may be, for example, 1.0 mm, and the materials of the top layer may include, for example, polycarbonate (PC), polymethyl methacrylate (PMMA) and the like. The sample injection unit (100) and the microfluidic channel (110) are provided within the top layer, and the sample inject unit (100) and the microfluidic channel (110) can be formed through a patterning process using micro-milling. The portion of the top layer where the detection unit (120, 120') is positioned may be variously modified and changed so that the detection unit (120, 120') can be inserted, including a concave portion in conformity with the shape of the detection unit (120, 120'). Also, the depth of the concave portion can be variously modified and changed according to the environment in which the present invention actually implemented. The bottom layer is not patterned but is a pressure sensitive adhesion layer that can be bonded to the top layer. The material thereof may include, for example, a polyolefin series and the like.

FIG. 3C illustrates each layer of the rotatable platform (10) comprising the microfluidic structures (20") of FIG. 1G. As shown in FIG. 3C, the rotatable platform (10) including the microfluidic structures (20") is mainly composed of three layers, each of which corresponds to the top layer wherein the sample injection unit (100) and the microfluidic channel (110) are positioned, a bottom layer (see FIG. 4D) for inserting the detection unit, and a PSA (Pressure sensitive adhesion) layer for bonding the top and bottom layers. The materials of the top and bottom layers may include, for example, polycarbonate (PC), polymethyl methacrylate (PMMA) and the like. The sample injection unit (100) and the microfluidic channel (110) are provided within the top layer, and the sample injection unit (100) and the microfluidic channel (110) can be formed through a patterning process using micro-milling. The portion of the top layer where the detection unit (120') is positioned may be variously modified and changed so that the detection unit (120') can be inserted, including a concave portion in conformity with the shape of the detection unit (120'). Also, the depth of the concave portion can be variously modified and changed according to the environment in which the present invention is actually implemented. A hydrophilic material is coated on the inside of the microfluidic channel (110) to receive the fluid sample containing the heavy metals. To have a space in which the detection unit (120') can be inserted in the bottom layer, the lower surface of the top layer may include a concave portion in conformity with the shape of the detection unit (120'). The ruler (130) is patterned in the bottom layer. The PSA layer is an adhesive layer serving to bond the top layer and the bottom layer, and can be formed into, for example, an acryl based double-sided adhesive tape in a tape or a plate having an adhesive component corresponding to the size of the rotatable platform (10), the region corresponding to the sample injection unit (100) and the microfluidic channel (110) in the top layer, and the region corresponding to the detection unit (120') in the bottom layer may be removed by cutting or the like. On the other hand, the top layer and the PSA layer are made of a transparent material so ha the development of the sample in the detection unit (120") and the ruler in the bottom layer can be identified. However, the present invention is not limited to the above-described embodiments, and various modifications and changes are possible, for example, the ruler (130) may be patterned on the top layer.

FIGS. 4A to 4D illustrate each layer of the rotatable platform (10) comprising the microfluidic structures (20''') of FIG. 2A. As shown in FIG. 4A, the rotatable platform (10) including the microfluidic structures (20") is mainly composed of three layers, each of which corresponds to the top layer wherein the sample injection unit (100) and the microfluidic channel (110) are positioned (see FIG. 4B), a bottom layer (see FIG. 4D) for inserting the detection unit, and a PSA (Pressure sensitive adhesion) layer (see FIG. 4C) for bonding the top and bottom layers. In FIGS. 4A to 4D, the description of the device for qualitative analysis and quantitative analysis (1''') of FIG. 2A and the microfluidic structures (20''') of FIG. 2B, and the respective layer that overlap with those in the device for qualitative analysis and quantitative analysis (1") of FIG. 1G and the microfluidic structures (20"), and the respective layer refers to the descriptions of FIG. 3C.

According to the device for qualitative analysis and quantitative analysis (1, 1', 1", 1''') of the present invention, the rotation of the device for qualitative analysis and quantitative analysis (1) is controlled so that the fluid sample containing the heavy metals moves from the sample injecting unit (100) into the microfluidic channel (110), and then moves to the detection unit (120, 120', 120"). For example, after the fluid sample containing the heavy metals is injected into the sample injection unit (100), when the device for qualitative analysis and quantitative analysis (1, 1', 1", 1''') is first rotated for 10 seconds at 3000 RPM and then stopped, the fluid sample containing the heavy metals moves to the microfluidic channel (110). When the device for qualitative analysis and quantitative analysis (1, 1', 1", 1''') is secondarily rotated at 5,000 RPM for 5 seconds, the fluid sample containing the heavy metals in the microfluidic channel (110) of the top layer is injected to the detection unit (120, 120', 120") inserted in the bottom layer by the centrifugal force. When the rotation of the device for qualitative analysis and quantitative analysis (1, 1', 1", 1''') is stopped, the fluid sample containing the heavy metals is developed on the detection units (120, 120', 120") by the capillary force.

The fluid sample including the heavy metals developed on the detection unit (120, 120', 120") reacts with the reagents previously coated on the detection unit (120, 120', 120") to indicate colors related to the heavy metals. As an organic substance that can be previously applied to the detection unit (120, 120', 120"), for example, an organic chelating agent may be used. In one embodiment, organic substances based on a reaction list between heavy metal ions and the organic chelating agents as shown in Table 1 below may be used.

TABLE 1

| Heavy Metals | Form | Chelating agent (concentration) |
| --- | --- | --- |
| Nickel ($Ni^{2+}$) | Sulfate | Dimethylglyoxime (100 mM) |
| Iron ($Fe^{2+}$) | Sulfate | Bathophenanthroline (5 mM) |
| Copper ($Cu^{2+}$) | Sulfate | Dithiooxamide (20 mM) |
| Mercury ($Hg^{2+}$) | Sulfate | Dithizone (5 mM) |
| Chromium ($Cr^{6+}$) | Oxide | Diphenylcarbazide (10 mM) |
| Zinc ($Zn^{2+}$) | Sulfate | 1-(2-Pyridylazo)-2-naphthol (5 mM) |

FIG. 5 shows the color development reaction between heavy metal ions and the organic chelating agents according to Table 1. In the embodiment of FIG. 5, PAN (1-(2-pyridylazo)-2-naphthol), Bphen (bathophenanthroline), DMG (dimethylglyoxime), DTO (dithiooxamide), DCB (diphenylcarbazide) and DTZ (dithizone) were used as the organic chelating agents. And 1% $H_2SO_4$ was added to DCB for $Cr^{6+}$ to improve the reaction selectivity of $Cr^{6+}$ ion for DCB and the color development reaction.

The device for qualitative analysis and quantitative analysis (1, 1') according to the present invention can provide a simultaneous qualitative analysis up to a level of 25 ppm for a plurality of the heavy metals such as $Fe^{2+}$, $Zn^{2+}$, $Hg^{2+}$, $Ni^{2+}$, or $Cu^{2+}$ within 15 minutes.

The qualitative analysis can be performed on the heavy metals contained in the fluid sample with the hue according to the color development reaction on the detection unit (120, 120', 120"). For example, when the hue according to the color development reaction is observed with the naked eyes, the types of the heavy metals contained in the fluid sample can be identified. FIG. 6 shows an example of a simultaneous qualitative analysis for six heavy metals (100 ppm) using the device for qualitative analysis and quantitative analysis (1''') of FIG. 2A.

In addition, the degree of development of the fluid sample including the heavy metals on the detection unit (120, 120', 120") can be quantitatively analyzed by using the ruler (130). Referring to the example of FIG. 6, it can be seen that the degree of development of the fluid sample including the heavy metals on the detection unit (120") of each of the plurality of the microfluidic structures (20''') is different from each other. It is possible to measure the extent to which a fluid sample containing the heavy metals is developed by using the respective ruler (130). The development distance of the corresponding fluid sample on the detection unit (120) is measured using the ruler (130), the types of heavy metals contained in the fluid sample are determined by the above qualitative analysis, and the quantitative analysis of the heavy metals can be performed by substituting the development distance into a calibration curve for the heavy metals (see FIGS. 7A and 7B). As an example of the quantitative analysis, FIG. 7A shows a case where $Cr^{6+}$ is quantitatively analyzed and FIG. 7B shows a case where $Fe^{2+}$ is quantitatively analyzed using the device for qualitative analysis and quantitative analysis (1''') of FIG. 2A. For example, the numbers of 1 ppm, 5 ppm, 10 ppm, 25 ppm, 50 ppm, and 100 ppm described in FIG. 7A are the results of quantitative analysis of $Cr^{6+}$. This is a method in which the degree of purple development corresponding to $Cr^{6+}$ on the six detection units (120") is measured using the ruler (130) and then the measured development distance is substituted into the calibration curve of $Cr^{6+}$ to obtain the concentration on the x axis corresponding to the degree of development on the y axis of the calibration curve so as that the quantitative analysis of $Cr^{6+}$ can be performed. In the case of $Fe^{2+}$ in FIG. 7B, the quantitative analysis can be performed the same manner. At this time, in the case of $Cr^{6+}$, the detection limit of the qualitative analysis is 1 ppm and the detection limit of the quantitative analysis is 5 ppm. In the case of $Fe^{2+}$, the detection limit of the qualitative analysis is 25 ppm and the detection limit of the quantitative analysis is 50 ppm.

Hereinafter, with reference to FIG. 8, a method (2) of analyzing a fluid sample containing the heavy metals using the device for qualitative analysis and quantitative analysis (1, 1', 1", 1''') according to one embodiment of the present invention will be described. The steps of the method for analyzing a sample (2) according to an embodiment of the present invention are as follows:

Step 1: Injecting a fluid sample into the sample injection unit (100) of the device for qualitative analysis and quantitative analysis (1, 1', 1", 1''') (S1);

Step 2: Controlling the rotation of the device for qualitative analysis and quantitative analysis (1, 1', 1", 1''') (S2); and Step 3: Performing at least one of qualitative analysis and quantitative analysis (S3).

Step 1: Injecting a Fluid Sample into the Sample Injection Unit (100) of the Device for Qualitative Analysis and Quantitative Analysis (1, 1', 1", 1''') (S1)

The fluid sample is injected into each sample injection unit (100) of the plurality of the microfluidic structures (20) of the device for qualitative analysis and quantitative analysis (1, 1', 1", 1'''). For example, about 40 μl of the fluid sample each can be injected into each sample injection unit (100). However, the present invention is not limited to this embodiment, and the amount of the injection can be variously adjusted according to various environments in which the present invention is implemented. The fluid sample containing different kinds of the heavy metals are respectively injected into each of the plurality of the microfluidic structures (20, 20', 20", 20''') (S1-1) to perform qualitative analysis and/or quantitative analysis as described below, and the fluid sample containing the same kind of the heavy metals of varying concentrations are respectively injected into each of the microfluidic structures (20, 20', 20", 20''') (S1-2) to perform qualitative analysis and/or quantitative analysis as described below.

Step 2: Controlling the Rotation of the Device for Qualitative Analysis and Quantitative Analysis (1, 1') (S2)

The device for qualitative analysis and quantitative analysis (1, 1', 1", 1''') is mounted on a system for qualitative analysis and quantitative analysis (3) capable of rotating the device for qualitative analysis and quantitative analysis (1, 1', 1", 1'''), for example, a rotatable system for qualitative analysis and quantitative analysis (3) as shown in FIG. 9, and the device for qualitative analysis and quantitative analysis (1, 1', 1", 1''') is rotated. This step (S2) includes the following detailed steps:

Step 2-1: The device for qualitative analysis and quantitative analysis (1, 1', 1", 1''') is initially rotated at 2000 to 4000 RPM for 5 to 20 seconds and then is stopped to move the fluid sample including the heavy metals injected into the sample injection unit (100) located at the top layer of the microfluidic structure (20, 20', 20", 20''') to the microfluidic channel (110) (S2-1).

Step 2-2: The device for qualitative analysis and quantitative analysis (1, 1', 1", 1''') is secondarily rotated at 4000 to 6000 RPM for 3 to 10 seconds to flow the fluid sample including the heavy metals transferred to the microfluidic channel (110) at step 2-1 into the reservoir region (124, 150) of the microfluidic structures (20, 20', 20", 20''') (S2-2).

Step 2-3: The rotation of the device for qualitative analysis and quantitative analysis (1, 1', 1", 1''') is stopped so that the fluid sample including the heavy metals are guided by the capillary force to be developed on the detection unit (120, 120', 120") (S2-3).

Step 3: Performing at Least One of Qualitative Analysis and Quantitative Analysis (S3)

A qualitative analysis can be performed on the fluid sample developed on the detection unit (120, 120', 120") by a method of analyzing the color development reaction on the detection unit (120, 120', 120") with the naked eyes (S3-1), or a quantitative analysis can be performed by measuring the degree of development of the fluid sample developed on the detection unit (120, 120', 120") by using a ruler (130) and then substituting the measured values to the calibration curves of the corresponding heavy metals developed on the scale (S3-2), or both of the qualitative analysis and the quantitative analysis can be performed (S3-1 and S3-2). Examples related to this are described above with reference to FIGS. 6, 7A and 7B.

In summary, the device for qualitative analysis and quantitative analysis (1, 1', 1", 1''') according to an embodiment of the present invention includes the microfluidic structures (20) having the same structure that can detect a plurality of types (for example, six kinds) of the heavy metals on the rotatable platform (10) (for example, a circular disk), wherein each microfluidic structure (20) is arranged radially and symmetrically along the rotational direction of the rotatable platform (10) and comprises the detection unit (120, 120', 120") coated with an organic substance that can cause a color development reaction with the heavy metals.

According to the device for qualitative analysis and quantitative analysis (1, 1', 1", 1''') and the method of analyzing the sample using the same (2) according to the embodiment of the present invention, the centrifugal force generated upon rotation of the device for qualitative analysis and quantitative analysis (1, 1', 1", 1''') can move the fluid sample containing the heavy metals to the detection unit (120, 120', 120") and the qualitative analysis can be performed through the color development reaction. Further, the fluid can be developed by the paper capillary force when the rotation of the device stops and the quantification may be performed by identifying the color developed distance with the ruler (130) patterned on the device for qualitative analysis and quantitative analysis (1, 1', 1", 1'''). It is possible to increase the detection limit of the heavy metals through automatic fluid control and control of torque and capillary force. It is possible to improve the detection limit of the heavy metal ions by the torque control. That is, by adjusting the centrifugal force and the capillary force by the rotation control, it is possible to improve the detection limit by controlling the reaction time of color development and the colored area. Specifically, on the detection unit, when the development speed of the sample containing the heavy metals due to the capillary force becomes faster than the speed at which the heavy metals and the organic chelating agent react with each other, the sample containing the heavy metals fails to sufficiently react with the organic chelating agent and develops on the entire detection unit. In the case of a heavy metal sample having a high concentration, there is no problem in detection because of the color development, but there is a possibility that the quantitative property is lowered. In the case of a heavy metal sample having a low concentration, there is a possibility that the detection sensitivity and limit are lowered because the sample fails to sufficiently react with the organic chelating agent on the detection unit, and thus the color development does not occur. However, according to the present invention, since the centrifugal force acts on the opposite side of the capillary force, the centrifugal force is applied to control the solution development speed by the capillary force so that the color development reaction can be sufficiently performed on the detection unit to improve the detection limitations.

Further, according to the device for qualitative analysis and quantitative analysis (1, 1', 1", 1''') and the method of analyzing the sample (2) using the same according to the embodiment of the present invention, it is economical and quick in the qualitative/quantitative analysis of multiple heavy metals. It is more economical than conventional expensive spectroscopy or mass spectrometry based heavy metal detector and can shorten analysis time. Thus, it can be applied quickly and conveniently in the field where the qualitative/quantitative analysis of heavy metals is required.

The technical constitution of the present invention as described above will be understood by those skilled in the art that various changes in form and details may be made therein without departing from the spirit and scope of the invention. It is therefore to be understood that the above-described embodiments are illustrative in all aspects and not restrictive. In addition, the scope of the present invention is indicated by the appended claims rather than the detailed description of the invention. Also, all changes or modifications derived from the meaning and scope of the claims and their equivalents should be construed as being included within the scope of the present invention.

EXPLANATION OF REFERENCE NUMBERS

1, 1', 1", 1''': Device for qualitative analysis and quantitative analysis
2: Method of analyzing a sample
3: System for qualitative analysis and quantitative analysis
10: Rotatable platform
20, 20', 20", 20''': Microfluidic structure
100: Sample injection unit
110: Microfluidic channel
120, 120', 120": Detection unit
130: Ruler

What is claimed is:

1. A device for qualitative analysis and quantitative analysis comprising a rotatable platform and a plurality of microfluidic structures disposed radially and symmetrically on the rotatable platform, wherein each of the plurality of the microfluidic structures comprises:

a sample injection unit configured to receive an injection of a respective fluid sample containing heavy metals, an entirety of the sample injection unit being located in a top layer of the rotatable platform, the sample injection unit including a space configured to receive an entirety of the respective fluid sample stored therein and an opening configured to receive the injection of the respective fluid sample;

a microfluidic siphon channel which is a passage providing fluid communication between the sample injection unit and one end of a detection unit;

the detection unit comprising a plurality of detection members each being coated with a respective different reagent, each reagent containing a different organic material, each organic material containing organic ligands configured to produce a color development reaction with the heavy metals of the fluid sample; and a ruler configured to measure a color developed distance of the color development reaction, the ruler being positioned alongside the detection unit, wherein each of the plurality of the microfluidic structures is configured to receive a different kind of the respective fluid samples than other ones of the plurality of the microfluidic structures, wherein the device is configured to move the respective fluid samples from the respective sample injection unit to the respective microfluidic channel and then to the respective detection unit when the rotatable platform is rotated, wherein the device is configured to provide the qualitative analysis of the fluid samples through the respective color development reaction of the heavy metals in the respective detection unit and the device is configured to provide the quantitative analysis of the fluid samples through measurement of the respective color developed distances, wherein each detection unit comprises a respective reservoir area which connects one end of each of the plurality of the detection members with the respective microfluidic channel, each of the detection members of each detection unit comprises a respective plurality of three or more sections coated with the respective different reagent, each section being coated with the respective organic material having different respective concentrations of the organic ligands, an entirety of each section being coated with the respective organic material having the different respective concentrations of the organic ligands, each of the detection members comprising a respective development area coated with the respective organic material configured to produce the color development reaction with the heavy metals of the respective fluid sample so that the respective fluid sample is developed, wherein the development area of each detection member is located closer to a center of the rotatable platform than the reservoir area of the respective detection unit, such that each detection member is configured to move the respective fluid sample from the respective reservoir to the respective development area in a direction from a periphery of the rotatable platform towards the center of the rotatable platform via a capillary force, and the plurality of sections of each detection member being disposed adjacent to one another along a longitudinal direction of the detection member, the plurality of sections of each detection member being configured to receive a respective portion of a respective one of the fluid samples flowing successively through the sections from a first section closest to the respective reservoir area towards a last section farthest from the respective reservoir area, the first section of each development area being coated with a highest concentration of the organic ligand, the plurality of sections of each detection member being continuously arranged so that boundaries thereof are in contact with each other along the longitudinal direction of the detection member.

2. The device according to claim 1, wherein the concentration of the organic ligands of the organic material coated in the section of each detection member located i-th from the respective reservoir area is lower than the concentration of the organic ligands of the organic material coated in the section located i-1-th from the respective reservoir area, wherein i is a natural number from 1 to n.

3. The device according to claim 1, further comprising a respective air circulation channel connecting each sample injection unit and another end of each respective detection unit, wherein each air circulation channel is configured to increase a rate of evaporation of the fluid sample in the respective detection unit and is configured to prevent a moisture condensation phenomenon in the respective detection unit.

4. The device according to claim 1, wherein the device is configured to move the respective fluid samples by:
a first rotation of the rotatable platform and then stopping the first rotation so that the fluid sample injected into each respective sample injection unit is moved to the respective microfluidic siphon channel;
a second rotation of the rotatable platform so that the fluid sample moved to each respective microfluidic channel is moved to the respective reservoir area; and
stopping rotation of the rotatable platform so that the fluid sample moved to each respective reservoir area is developed in the detection unit.

5. The device according to claim 4, wherein each microfluidic siphon channel includes a portion of a "U" shaped tube that is configured to receive the respective fluid sample after the first rotation and before the second rotation of the rotatable platform.

6. The device according to claim 4, wherein the first rotation of the rotatable platform is performed at 2000 to less than 4000 RPM for 5 to 20 seconds and the second rotation of the rotatable platform is performed at 4000 to 6000 RPM for 3 to 10 seconds.

7. The device according to claim 1, wherein the heavy metals included in each of the fluid samples comprise $Fe^{2+}$, $Zn^{2+}$, $Hg^{2+}$, $Cr^{6+}$, $Ni^{2+}$, or $Cu^{2+}$.

8. The device according to claim 7, wherein the organic material that coats the detection units comprises any one selected from the group consisting of dimethylglyoxime, bathophenanthroline, dithiooxamide, dithizone, diphenylcarbazide and 1-(2-pyridylazo)-2-naphthol.

9. The device according to claim 1, wherein, within each detection member, the last section has a lowest one of the respective concentrations.

10. A method of analyzing the fluid samples by using the device according to claim 1, the method comprising:
injecting each fluid sample into the respective sample injection unit;
rotating the rotatable platform; and
performing at least one of the qualitative analysis and the quantitative analysis of the fluid sample developed in each respective detection unit.

11. The method according to claim 10, wherein the injecting of each fluid sample into the respective sample injection unit comprises:
injecting a first amount of each fluid sample into the respective one of the microfluidic structures; or
injecting a second amount of each fluid sample into the respective one of the microfluidic structures, the first amount of each fluid sample having a different concentration than the second amount of each fluid sample.

12. The method according to claim 10, wherein the performing of the at least one of the qualitative analysis and the quantitative analysis of each fluid sample comprises:
performing the at least one of the qualitative analysis through the color development reaction of each sample developed in the respective detection unit and the quantitative analysis through the measurement of the respective color developed distance.

13. A method of analyzing the fluid samples by using the device according to claim 1, the method comprising:
injecting each fluid sample into the respective sample injection unit;
rotating the rotatable platform; and performing at least one of the qualitative analysis and the quantitative analysis of the fluid sample developed in each respective detection unit, wherein the rotating of the rotatable platform comprises:

rotating the rotatable platform firstly and then stopping the rotating so that the fluid sample injected into each respective sample injection unit is moved to the respective microfluidic channel;

rotating the rotatable platform secondarily so that the fluid sample moved to each microfluidic channel is moved to the respective reservoir area; and stopping the rotation of the rotatable platform so that the sample moved to each reservoir area is developed in the respective detection unit.

\* \* \* \* \*